US010005815B2

(12) United States Patent
Carlson et al.

(10) Patent No.: US 10,005,815 B2
(45) Date of Patent: Jun. 26, 2018

(54) BIOLOGICALLY CLEAVABLE TETRAPEPTIDE LINKING AGENTS

(71) Applicant: Arrowhead Madison Inc., Madison, WI (US)

(72) Inventors: Jeffrey C. Carlson, Madison, WI (US); Andrei V. Blokhin, Fitchburg, WI (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 0 days. days.

(21) Appl. No.: 15/166,323

(22) Filed: May 27, 2016

(65) Prior Publication Data

US 2016/0347793 A1   Dec. 1, 2016

Related U.S. Application Data

(60) Provisional application No. 62/168,244, filed on May 29, 2015, provisional application No. 62/235,833, filed on Oct. 1, 2015.

(51) Int. Cl.
| | |
|---|---|
| *A61K 38/06* | (2006.01) |
| *A61K 38/07* | (2006.01) |
| *C07K 5/103* | (2006.01) |
| *C07K 5/107* | (2006.01) |
| *A61K 38/00* | (2006.01) |

(52) U.S. Cl.
CPC ............ *C07K 5/1008* (2013.01); *C07K 5/101* (2013.01); *C07K 5/1016* (2013.01); *A61K 38/00* (2013.01)

(58) Field of Classification Search
CPC ................................ A61K 38/00; A61K 38/07
See application file for complete search history.

(56) References Cited

U.S. PATENT DOCUMENTS

| | | |
|---|---|---|
| 6,214,345 B1 | 4/2001 | Firestone et al. |
| 7,589,170 B1 | 9/2009 | Smythe et al. |
| 8,084,599 B2 | 12/2011 | Rossi et al. |
| 8,137,695 B2 | 3/2012 | Rozema et al. |
| 8,349,809 B2 | 1/2013 | Brown |
| 8,426,554 B2 | 4/2013 | Rozema et al. |
| 8,513,207 B2 | 8/2013 | Brown |
| 8,802,773 B2 | 8/2014 | Rozema et al. |
| 2008/0214648 A1 | 9/2008 | De Kock et al. |
| 2015/0045573 A1 | 2/2015 | Cheng et al. |

FOREIGN PATENT DOCUMENTS

| | | | | |
|---|---|---|---|---|
| WO | 2000047608 A1 | 8/2000 | | |
| WO | 2009117531 A1 | 9/2009 | | |
| WO | WO 2014052650 A2 * | 4/2014 | ................ | C07K 7/06 |
| WO | WO 2014200910 A2 * | 12/2014 | ............ | A61K 39/098 |

OTHER PUBLICATIONS

Bachem, Periodic Chart of Amino Acids, Poster, accessed online at: https://images.sampletemplates.com/wp-content/uploads/2016/02/11114513/Periodic-Chart-of-Amino-Acid.zip, on May 22, 2017.*
Nollmann et al., Angew. Chem. Int. Ed., 2013, 52, 7597-7599.*
Masa et al., Biochemistry 2006, 45, 15474-15482.*
Amir et al.; "Domino Dendrimers"; Adv. Polym. Sci.; (2006); 192: 59-93.
Carl et al. "A novel connector linkage applicable in prodrug design", Journal of Medicinal Chemistry, 24(5), 1981, pp. 479-480.
Carlson et al.; Enzyme Sensitive Conjugates as a Macromolecular Delivery Platform for siRNA; Arrowhead Madison Inc; (2015).
Choi Ki et al.; "Protease-Activated Drug Development"; Theranostics; 2012; 2(2):156-178.
Chu et al.; "Cathepsin B-sensitive polymers for compartment-specific degradation and nucleic acid release"; J Control Release; 2012; 157(3): 445-454.
Dorywalska et al.; "Effect of Attachment Site on Stability of Cleavable Antibody Drug Conjugates"; 2015; pp. 650-659.
Elsadek et al.; "Optimization of an Albumin-Binding Prodrug of Doxorubicin That Is Cleaved by Prostate-Specific Antigen"; ACS Med. Chem. Lett.; 2010; 1; 234-238.
Florent et al.; "Prodrugs of Anthracyclines for Use in Antibody-Directed Enzyme Prodrug Therapy"; J. Med. Chem.; 1998; 41; 3572-3581.
Gopin et al.; "Enzymatic Activation of Second-Generation Dendritic Prodrugs: Conjugation of Self-Immolative Dendrimers with Poly(ethylene glycol) via Click Chemistry"; Bioconjugate Chem.; 2006; 17; 1432-1440.
Graham et al.; "Isolation of Lysosomes from Tissues and Cells by Differential and Density Gradient Centrifugation"; Current Protocols in Cell Biology; 2000; 3.6.1-3.6.21.
Greenwald et al.; "Drug Delivery Systems Employing 1,4- or 1,6-Elimination: Poly(ethylene glycol) Prodrugs of Amine-Containing Compounds"; J. Med. Chem.; 1999; 42; 3657-3667.
Greenwald et al.; "Drug Delivery Systems Based on Trimethyl Lock Lactonization: Poly(ethylene glycol) Prodrugs of Amino-Containing Compounds"; J. Med. Chem.; 2000; 43; 475-487.
Iobst, S.T. and Drickamer, K., J.B.C., 1996, 271, 6686.
Malugin et al.; "Liberation of doxorubicin from HPMA copolymer conjugate is essential for the induction of cell cycle arrest and nuclear fragmentation in ovarian carcinoma cells"; Journal of Controlled Release; 124; 2007; pp. 6-10.
Masquelier et al.; "Amino Acid and Dipeptide Derivatives of Daunorubicin. 1. Syntheses, Physicochemical Properties, and Lysosomal Digestion"; American Chemical Society; 1980; pp. 1166-1170.
Miller et al.; "Targeting Bone Metastases with a Bispecific Anticancer and Antiangiogenic Polymer-Alendronate-Taxane Conjugate"; Angew. Chem. Int. Ed.; 2009; 48; 2949-2954.
Monera et al.; "Relationship of Sidechain Hydrophobicity and α-Helical Propensity on the Stability of the Single-stranded Amphipathic α-Helix"; Journal of Peptide Science; vol. 1; 319-329; (1995).
Reboud-Ravaux et al.; "Quinone Methides and AZA-Quinone Methides as Latent Alkylating Species in the Design of Mechanism-Based Inhibitors of Serine Proteases and β-Lactamases"; Quinone Methides; Edited by Steven E. Rokita; 2009; pp. 357-383.
Rejmanova et al.; Makromol. Chem.; 184; 2009-2020; (1983).
Riches AG et al., Tetrahedron, 2012, 68, pp. 9448-9455.

(Continued)

*Primary Examiner* — Hasan S Ahmed
*Assistant Examiner* — Kaipeen E Yang
(74) *Attorney, Agent, or Firm* — Robert Michael Teigen

(57) ABSTRACT

Tetrapeptide linkers for reversibly linking a first compound to a amine-containing second compound are described. Compounds containing the tetrapeptide linkers and methods of using the tetrapeptide linkers are also described.

21 Claims, 3 Drawing Sheets

(56) References Cited

OTHER PUBLICATIONS

Rozema et al.; "Protease-triggered siRNA delivery vehicles"; Journal of Controlled Release 209; (2015); 57-66.

Schmid et al.; "Albumin-Binding Prodrugs of Camptothecin and Doxorubicin with an Ala-Leu-Ala-Leu-Linker That are Cleaved by Cathepsin B: Synthesis and Antitumor Efficacy"; Bioconjugate Chem.; 2007; 18; 702-716.

Schmid et al.- "Development of Albumin-Binding Camptothecin Prodrugs Using a Peptide Positional Scanning Library"; Bioconjugate Chem.; 2007; 18; 1786-1799.

Shamis et al.; "Bioactivation of Self-Immolative Dendritic Prodrugs by Catalytic Antibody 38C2"; J. Am. Chem. Soc.; 2004; 126; 1726-1731.

Soler et al.; "Enzyme-triggered delivery of chlorambucil from conjugates based on the cell-penetrating peptide BP16"; Org. Biomol. Chem.; 2015; 13; 1470-1480.

Toki et al. "Protease-Mediated fragmentation of p-Amidobenzyl Ethers: A New Strategy for the Activation of Anticancer Prodrugs", J. Org. Chem., 2002, 67, 1866-1872.

Trouet et al.; "A covalent linkage between daunorubicin and proteins that is stable in serum and reversible by lysosomal hydrolases, as required for a lysosomotropic drug-carrier conjugate: In vitro and in vivo studies"; Proc. Natl. Acad. Sci. USA; vol. 79; pp. 626-629; 1982.

Zhang et al.; "Chain-Shattering Polymeric Therapeutics with On-Demand Drug-Release Capability"; Angew. Chem. Int. Ed.; 2013; 52; 6435-6439.

Zhang et al.; "Anti-Cancer Effects of Novel Doxorubicin Prodrug PDOX in MCF-7 Breast Cancer Cells"; J. Huazhong Univ. Sci. Technol; 34(4):521-528; 2014.

Zhong et al.; "Cathepsin B-cleavable doxorubicin prodrugs for targeted cancer therapy"; International Journal of Oncology; 42; 373-383; 2013.

Basse et al.; "Novel Organic Proteasome Inhibitors Identified by Virtual and in Vitro Screening"; Journal of Medicinal Chemistry; 2010; 53; 509-513.

De Groot et al.; "Synthesis and Biological Evaluation of Novel Prodrugs of Anthracyclines for Selective Activation by the Tumor-Associated Protease Plasmin"; J. Med. Chem.; 1999; 42; 5277-4283.

Dubowchik et al.; "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity"; Bioconjugate Chem.; 2002; 13; 855-869.

International Preliminary Report on Patentability for corresponding International Application No. PCT/US2016/034517 dated Dec. 5, 2017.

International Search Report and Written Opinion for corresponding International Application No. PCT/US2016/034517 dated Oct. 28, 2016.

\* cited by examiner

NAG(OR)₃

PEG₁₂

PGA

AENA

EDANS

R = Acetyl or H,

R¹ = A⁴ or A³ or A³⁻⁴

R² = A¹

R³ = PGA or PABC

R⁴ = EDANS

A.

B.

BIOLOGICALLY CLEAVABLE TETRAPEPTIDE LINKING AGENTS

PRIORITY

This application claims priority to U.S. Provisional Patent Application No. 62/168,244, filed May 29, 2015, and U.S. Provisional Patent Application No. 62/235,833, filed Oct. 1, 2015, the contents of both of which are incorporated herein by reference.

SEQUENCE LISTING

This application contains a Sequence Listing which has been submitted electronically in ASCII format. The ASCII copy, created on May 18, 2016, is named "30630-US1_SequenceListing_ST25" and is 5 kb in size.

BACKGROUND

Physiologically labile linkers or modifiers are useful for a variety of process, including therapeutic drug delivery. The utility of the linker or modifier may be further enhanced if cleavage of the linker regenerates at least one of the original components in an unmodified state without any vestige of the linker or modifier.

Several strategies have been investigated in clinical and preclinical settings to reversibly link or modify a compound. Such reversible conjugates are used to lessen toxic effects and improve pharmacological properties of the compound. To be effective, the reversible conjugate must remain stable in the bloodstream, yet allow for release of the compound after interaction of the conjugate with the target cell. Further, the cleavage of the linker or modifier must be such that the compound be allowed to reach its biochemical target and to interact effectively with it. Often, the compound must be released in an unmodified state.

Examples of reversible conjugates include prodrugs, derivatives of drugs which remain inactive in their prototype form but are metabolized in the body to generate the active drugs, and carriers such as antibody-drug conjugates. The formation of reversible conjugates has been shown to be useful in the development of antitumor chemotherapeutic drugs and in nucleotide delivery.

Rozema et al. (U.S. Pat. No. 8,137,695) have shown reversible modification of polyamines using dimethylmaleic anhydrides which form pH sensitive maleamide linkages. Delivery of the modified polymer to cells and internalization results in cleavage of the maleamide linkage in the reduced pH environment of endosomes to regenerate polymer amines.

In addition to pH sensitive linkages, peptide-containing linkages have been developed that are activated by proteases in vivo. Rozema et al. (U.S. Pat. No. 8,426,554) provided a means to reversibly regulate membrane disruptive activity of membrane active polyamines using steric stabilizers or targeting groups conjugated to polymeric amino-containing sidechains via a dipeptide p-amidobenzyl-carbamate spacer (PABC). According to the published design, in presence of proteolytic enzymes, hydrolysis of the anilide bond triggers a 1,6-elimination cascade that results in generation of a unmodified polycationic polymer with restored membranolytic properties.

Application of the self-immolative PABC spacer in pro-drug design was originally proposed by Carl et al. (1981). This strategy combines cleavage of covalent anilide bond with spontaneous release of the desired substrate. PABC spacers have been extensively studied for controlled drug release of a therapeutic agent, particularly for anticancer therapy (Dorywalska et al. 2015, Zhang et al. 2014, Florent et al 1998, Toki et al. 2002, Shamis et al. 2004, Amir et al. 2005, Amir et al. 2005, Gopin et al. 2006, Zhang et al. 2013, Zhang et al. 2013), However, there is concern that the aza-quinone methide, also known as a quinonimine methide (QIM), generated during PABC elimination, can be a source of toxicity due to its propensity to react with N, O, and S-nucleophiles (Reboud-Ravaux et al. 2009).

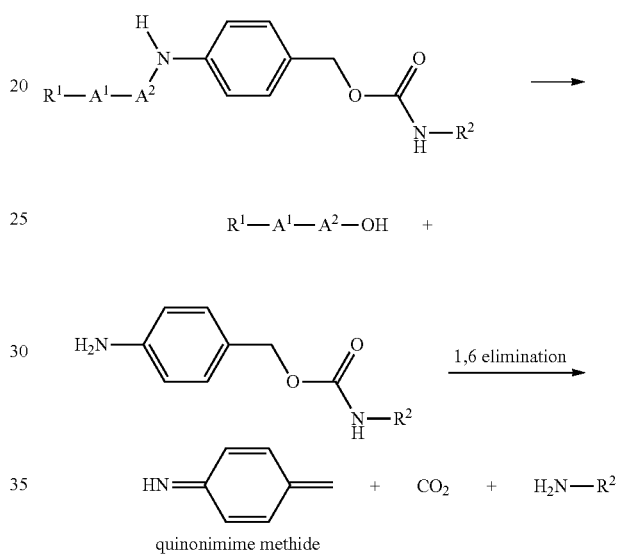

Certain peptide proteolyzable pro-drugs lacking the PABC spacer have been described (Zhong et al. 2013, Cho K Y et al. 2012). However, a limitation of the prior described peptide proteolyzable pro-drugs is that they do not liberate the primary amine constituent of the parent drug in a rate comparable to that of self-immolating PABC type analogues. Cleavage of the C-terminal amino acid residue by endopeptidases during proteolysis of the prodrug appears to be the rate limiting step (Masquelier et al. 1980, Schmid et al. 2007, Schmid et al. 2007, Elsadek et al. 2010, Trouet et al. 1982).

SUMMARY

Described herein are tetrapeptide linkers for reversibly linking a first compound to a amine-containing second compound. The physiologically cleavable linkers (linkers) comprise a tetrapeptide having the general from: $-A^4-A^3-A^2-A^1-$ wherein $A^4$ is a hydrophobic L-amino acid, $A^3$ is a hydrophilic L-amino acid, $A^2$ is a hydrophobic L-amino acid, and $A^1$ is L-proline, L-leucine, or L-N-methyl alanine. The tetrapeptide linkers are cleaved (digested) by proteolytic enzymes such as endogenous proteases present in an organism, particularly a mammal, tissue, cell, or subcellular compartment or organelle. Further, proteolytic enzymes readily and rapidly cleave the peptide bond on the C-terminal side of $A^1$ to liberate the amine-containing second compound. Further described are compositions containing the described tetrapeptide linkers and methods for using the tetrapeptides for reversibly linking two moieties or reversibly modifying an amine or amine-containing compound. The described reversible linkers and modifiers provide for serum stable modification and can be cleaved in vivo.

Described herein are tetrapeptide linking agents comprising: $R^5$-$A^4$-$A^3$-$A^2$-$A^1$-$R^7$, wherein $R^5$ comprises a first compound, $A^4$ is a hydrophobic L-amino acid, $A^3$ is a hydrophilic L-amino acid, $A^2$ is a hydrophobic L-amino acid, and $A^1$ is L-proline, L-leucine, or L-N-methyl alanine, and $R^7$ is an amine-reactive group. $R^7$ is chosen such that reaction with an amine or amine-containing compound forms an amide bond with $A^1$. In some embodiments, $A^3$ is a polar uncharged L-amino acid. In some embodiments, the tetrapeptide linking agents can be used to reversibly link the first compound to the amine-containing compound. In some embodiments, the tetrapeptide linking agents can be used to reversibly modify an amine-containing compound. In some embodiments, the tetrapeptide linking agents can be used to reversibly modify a polyamine. In some embodiments, the polyamine is a membrane active polyamine.

In some embodiments, we describe compositions comprising a first compound linked to a second compound via a tetrapeptide linking agent wherein the tetrapeptide linking agent consists of $A^4A^3A^2A^1$ wherein $A^4$ is a hydrophobic L-amino acid, $A^3$ is a hydrophilic L-amino acid, $A^2$ is a hydrophobic L-amino acid, $A^1$ is L-proline, L-leucine, or L-N-methyl alanine, and $A^1$ is linked to the second compound via an amide bond. In some embodiments, $A^3$ is a polar uncharged L-amino acid. Cleavage (digestion) of the tetrapeptide by proteolytic enzymes in vitro or in vivo results in cleavage between $A^1$ and the second compound to liberate the second compound. In some embodiments, $A^4A^3A^2A^1$ has the sequence: FCitFP (SEQ ID NO: 12), VCitFP (SEQ ID NO: 19), ACitFP (SEQ ID NO: 3), FKFP (SEQ ID NO: 16), FCitVP (SEQ ID NO: 13), FCitFL (SEQ ID NO: 11), FCitF(Nme)A (SEQ ID NO: 9), or FCitAP (SEQ ID NO: 8), wherein F is L-phenylalanine, Cit is L-citrulline, P is L-proline, V is L-Valine, A is L-alanine, K is L-Lysine, L is L-leucine, (Nme)A is L-N-methyl-alanine.

In some embodiments, compositions comprising reversibly modified polyamines are described. The polyamines are modified by reversible modification of a plurality of amines on the polyamine with the herein described tetrapeptide linking agents. In some embodiments, the polyamine is an amphipathic membrane active polyamine. In some embodiments, the composition further comprises an RNAi trigger. The polyamine can be covalently linked to the RNAi trigger. In some embodiments, the linkage for covalent attachment of the polyamine to the RNAi trigger contains a physiologically labile linkage such as a disulfide bond. In some embodiments, the polyamine is not covalently linked to the RNAi trigger and the RNAi trigger is covalently linked to a targeting group. In some embodiments, the composition further comprises a pharmaceutically acceptable excipient.

In some embodiments, methods for linking a first compound to a amine-containing second compound are described, the methods comprising: attaching the first compound to the amino-terminus of a tetrapeptide and forming an amide bond between the carboxy-terminus of the tetrapeptide and the amine-containing second compound, wherein the tetrapeptide has the amino acid sequence $A^4A^3A^2A^1$, wherein $A^4$ is a hydrophobic L-amino acid, $A^3$ is a hydrophilic L-amino acid, $A^2$ is a hydrophobic L-amino acid, and $A^1$ is L-proline, L-leucine, or L-N-methyl alanine. In some embodiments, $A^4$ is phenylalanine. In some embodiments, $A^3$ is a polar uncharged L-amino acid. In some embodiments, the polar uncharged amino acid is L-citrulline. In some embodiments, $A^2$ is phenylalanine. In some embodiments, $A^1$ is proline.

In some embodiments, the tetrapeptide linker or linking agent has the four amino acid sequence selected from the group consisting of: FCitFP (SEQ ID NO: 12), VCitFP (SEQ ID NO: 19), ACitFP (SEQ ID NO: 3), FKFP (SEQ ID NO: 16), FCitVP (SEQ ID NO: 13), FCitFL (SEQ ID NO: 11), FCitF(Nme)A (SEQ ID NO: 9), FCitAP (SEQ ID NO: 8), wherein F is L-phenylalanine, Cit is L-citrulline, P is L-proline, V is L-Valine, A is L-alanine, K is L-Lysine, L is L-leucine, (Nme)A is L-N-methyl-alanine.

Described herein is the use of Phenylalanine-Citrulline-Phenylalanine-Proline (FCitFP (SEQ ID NO: 12)) tetrapeptide to form a physiologically cleavable linker. The FCitFP linker is rapidly cleaved by proteolytic enzymes in a mammal, mammalian tissue, mammalian cell, or mammalian subcellular compartment or organelle. In some embodiments, an amine-containing compound is linked to the proline via an amide bond. The proline C-terminal amide bond is efficiently cleaved by proteases in vivo to release the amine-containing compound.

In some embodiments, the first compound can be selected from the group comprising: targeting group, cell receptor ligand, integrin ligand, RGD ligand, RGD mimic, asialoglycoprotein receptor (ASGPr) ligand, galactose, galactose derivative, N-acetylgalactosamine, folate, steric stabilizer, polyethylene glycol (PEG), polynucleotide, polymer, polyamine, antibody, drug product, hapten, digoxigenin, vitamin, biotin, fluorophore, antibody, monoclonal antibody, and antibody fragment.

In some embodiments, the amine-containing second compound can be selected from the group comprising: targeting group, cell receptor ligand, integrin ligand, RGD ligand, RGD mimic, asialoglycoprotein receptor (ASGPr) ligand, galactose, galactose derivative, N-acetylgalactosamine, folate, steric stabilizer, polyethylene glycol (PEG), polynucleotide, polymer, polyamine, antibody, drug product, hapten, digoxigenin, vitamin, biotin, antibody, monoclonal antibody, and antibody fragment.

In some embodiments, compositions for delivering an RNAi trigger to a cell in vivo comprising are described.

DETAILED DESCRIPTION

Figure 1:
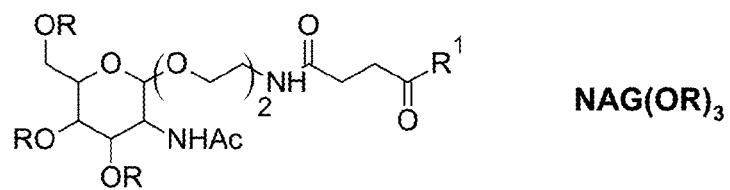
FIG. 1. Structures for some components used in preparation or testing of the described tetrapeptide linkers.
Figure 1:
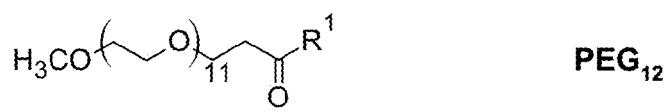
Figure 1:
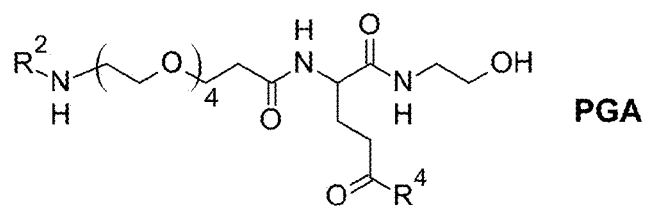
Figure 1:
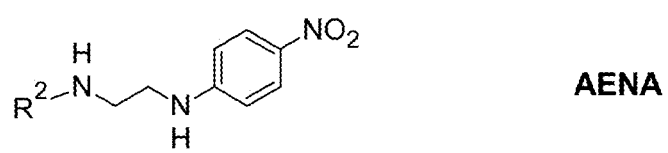
Figure 1:
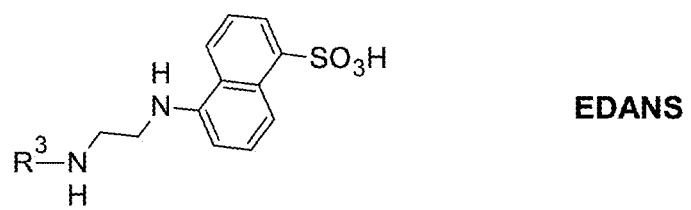

Described are tetrapeptide linkers and tetrapeptide linking agents useful for reversibly linking a first compound with an amine-containing second compound and/or reversibly modifying the amine-containing second compound. The described tetrapeptide linkers exhibit improved kinetics of cleavage over previously described peptide linkers used for prodrug delivery (Rejmanova et al. 1983, Malugin et al. 2007, Miller et al. 2009, Soler et al. 2015, Chu et al. 2012). The tetrapeptide linkers are stable to hydrolysis in absence of proteolytic enzymes. In the presence of proteolytic enzymes (also called proteinases, proteases, or peptidases) in vitro or in vivo, the tetrapeptide is readily cleaved. More specifically, the described tetrapeptide linkers and tetrapeptide linking agents are rapidly cleaved between the carboxy terminal amino acid of the tetrapeptide and the amine-containing second compound, releasing the amine-containing second compound.

In some embodiments, tetrapeptide linkers are described, the tetrapeptide linkers comprising the structure represented by:

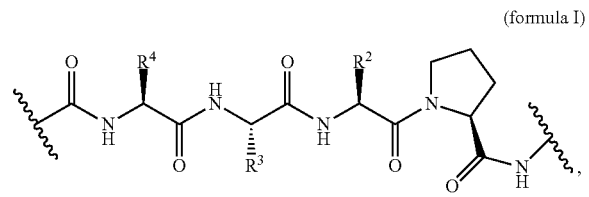

(formula I)

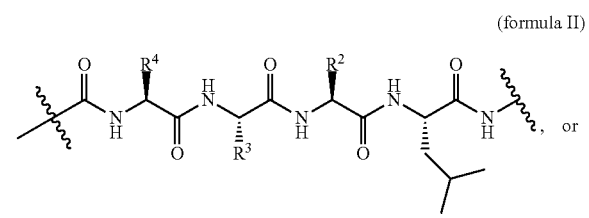

(formula II)

, or

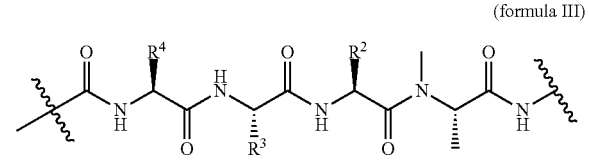

(formula III)

wherein,

R$^4$ is an R-group (side chain) of a natural, non-natural isomeric, or synthetic hydrophobic L amino acid wherein the hydrophobicity index (Monera et al, J. Protein Sci. 1995, 1, 319) at pH 7 is 41 or greater, normalized to glycine, as it relates to the composition of the amino acid side chain (R-group), R$^3$ is an R-group (side chain) of a uncharged hydrophilic or basic hydrophilic L amino acid wherein the hydrophobicity index (Monera et al, J. Protein Sci. 1995, 1, 319) at pH 7 is −28 or less, normalized to glycine, as it relates to the composition of amino acid side chain (R-group), and R$^2$ is an R group (side chain) of a natural, non-natural isomeric, or synthetic hydrophobic L amino acid wherein the hydrophobicity index (Monera et al, J. Protein Sci. 1995, 1, 319) at pH 7 is 41 or greater, normalized to glycine, as it relates to the composition of the amino acid side chain (R-group).

In some embodiments, R$^2$ and R$^4$ are independently selected from the group consisting of: —CH$_3$, —CH(CH$_3$)$_2$, —CH$_2$CH(CH$_3$)$_2$, —CH(CH$_3$)CH$_2$CH$_3$, and —CH$_2$C$_6$H$_6$.

In some embodiments, R$^3$ is selected from the group consisting of: —(CH$_2$)$_3$NHC(=O)NH$_2$, —CH$_2$CONH$_2$, —(CH$_2$)$_4$NH$_3$$^+$, and —(CH$_2$)$_3$—NH C(=NH)—NH$_2$. In some embodiments, R$^3$ is —(CH$_2$)$_3$NHC(=O)NH$_2$.

Following exposure to proteases in vivo, such as in a lysosome, the tetrapeptide C-terminal amide bond is rapidly cleaved (digested).

In some embodiments, the tetrapeptide linkers comprise the structure represented by:

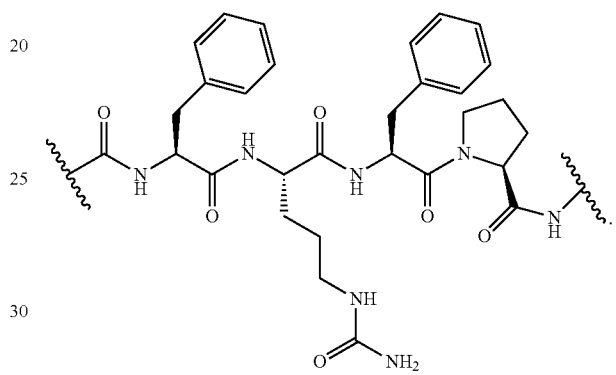

(formula XII)

In some embodiments, biologically labile compounds are described, wherein the biologically labile compounds include a first compound linked to an amine-containing second compound via a tetrapeptide linker comprising:

R$^5$-A$^4$-A$^3$-A$^2$-A$^1$-R$^6$ (formula IV)

wherein

R$^5$ represents the first compound,

R$^6$ represents the amine-containing second compound,

A$^4$ is a natural, non-natural isomeric, or synthetic hydrophobic L amino acid wherein the hydrophobicity index (Monera et al, J. Protein Sci. 1995, 1, 319) at pH 7 is 41 or greater, normalized to glycine, as it relates to the composition of the amino acid side chain (R-group), A$^3$ is an uncharged or basic hydrophilic L amino acid wherein the hydrophobicity index (Monera et al, J. Protein Sci. 1995, 1, 319) at pH 7 is −28 or less, normalized to glycine, as it relates to the composition of amino acid side chain (R-group), A$^2$ is a natural, non-natural isomeric, or synthetic hydrophobic L amino acid wherein the hydrophobicity index (Monera et al, J. Protein Sci. 1995, 1, 319) at pH 7 is 41 or greater, normalized to glycine, as it relates to the composition of the amino acid side chain (R-group), A$^1$ is L-proline, L-leucine, or L-N-methyl alanine, and A$^1$ is linked to R$^6$ via an amide bond.

In some embodiments, A$^1$ is L-proline, A$^2$ and A$^4$ are independently L-alanine, L-valine, L-leucine, L-isoleucine or L-phenylalanine (side chains of —CH$_3$, —CH(CH$_3$)$_2$, —CH$_2$CH(CH$_3$)$_2$, —CH(CH$_3$)CH$_2$CH$_3$, or —CH$_2$C$_6$H$_6$, respectively), and A$^3$ is L-citrulline, L-asparagine, L-lysine, or L-arginine (side chains of —(CH$_2$)$_3$NHCONH$_2$, —CH$_2$CONH$_2$, —(CH$_2$)$_4$NH$_3^+$, or —(CH$_2$)$_3$—NH—C(=NH)—NH$_2$, respectively).

In some embodiments, A$^1$ is L-proline, A$^2$ and A$^4$ are L-phenylalanine, and A$^3$ is L-citrulline (FCitFP (SEQ ID NO: 12)).

In some embodiments, A$^1$ is L-proline, A$^2$ is L-phenylalanine, A$^3$ is L-lysine, and A$^4$ is L-phenylalanine (FKFP (SEQ ID NO: 16)).

In some embodiments, A$^1$ is L-proline, A$^2$ is L-valine, A$^3$ is L-citrulline, and A$^4$ is L-phenylalanine (FCitVP (SEQ ID NO: 13)).

In some embodiments, A$^1$ is L-proline, A$^2$ is L-phenylalanine, A$^3$ is L-citrulline, and A$^4$ is L-valine (VCitFP (SEQ ID NO: 19)).

In some embodiments, A$^1$ is L-proline, A$^2$ is L-alanine, A$^3$ is L-citrulline, and A$^4$ is L-phenylalanine (FCitAP (SEQ ID NO: 8)).

In some embodiments, A$^1$ is L-proline, A$^2$ is L-phenylalanine, A$^3$ is L-citrulline, and A$^4$ is L-alanine (ACitFP (SEQ ID NO: 3)).

In some embodiments, A$^1$ is leucine, A$^2$ and A$^4$ are independently L-alanine, L-valine, L-leucine, L-isoleucine or L-phenylalanine (side chains of —CH$_3$, —CH(CH$_3$)$_2$, —CH$_2$CH(CH$_3$)$_2$, —CH(CH$_3$)CH$_2$CH$_3$, or —CH$_2$C$_6$H$_6$, respectively), and A$^3$ is L-citrulline, L-asparagine, L-lysine, or L-arginine (side chains of —(CH$_2$)$_3$NHCONH$_2$, —CH$_2$CONH$_2$—(CH$_2$)$_4$NH$_3^+$, or —(CH$_2$)$_3$—NH—C(=NH)—NH$_2$, respectively).

In some embodiments, A$^1$ is L-leucine, A$^2$ is L-phenylalanine, A$^3$ is L-citrulline, and A$^4$ is L-phenylalanine (FCitFL (SEQ ID NO: 11)).

In some embodiments, A$^1$ is L-N-methyl-alanine, A$^2$ and A$^4$ are independently L-alanine, L-valine, L-leucine, L-isoleucine or L-phenylalanine (side chains of —CH$_3$, —CH(CH$_3$)$_2$, —CH$_2$CH(CH$_3$)$_2$, —CH(CH$_3$)CH$_2$CH$_3$, or —CH$_2$C$_6$H$_6$, respectively), and A$^3$ is L-citrulline, L-asparagine, L-lysine, or L-arginine (side chains of —(CH$_2$)$_3$NHCONH$_2$, —CH$_2$CONH$_2$, (CH$_2$)$_4$NH$_3^+$, or —(CH$_2$)$_3$—NH—C(=NH)—NH$_2$, respectively).

In some embodiments, A$^1$ is L-N-methyl-alanine, A$^2$ is L-phenylalanine, A$^3$ is L-citrulline, and A$^4$ is L-phenylalanine (FCitF(Nme)A (SEQ ID NO: 9)).

In some embodiments, R$_5$ comprises a compound selected from the list comprising steric stabilizer, PEG, H—(CH$_2$)$_{0-2}$—(O—CH$_2$—CH$_2$)$_{1-500}$—O$_{0-1}$—(CH$_2$)$_{0-2}$—, PEG$_{1-100}$, targeting group, cell receptor ligand, integrin-binding ligand, RGD ligand, RGD mimic, asialoglycoprotein receptor (ASGPr) ligand, galactose, galactose derivative, N-acetylgalactosamine, folate, polynucleotide, polymer, polyamine, antibody, drug product, hapten, digoxigenin, vitamin, biotin, fluorophore, antibody, immunoglobulin, monoclonal antibody, and antibody fragment.

R$_6$ is a primary amine-containing compounds selected from the group comprising: steric stabilizer, PEG, H—(CH$_2$)$_{0-2}$—(O—CH$_2$—CH$_2$)$_{1-500}$—O$_{0-1}$—(CH$_2$)$_{0-2}$—, PEG$_{1-100}$, targeting group, cell receptor ligand, integrin-binding ligand, RGD ligand, RGD mimic, asialoglycoprotein receptor (ASGPr) ligand, galactose, galactose derivative, N-acetylgalactosamine, folate, polynucleotide, amine-modified polynucleotide, polymer, amine-containing polymer, polyamine, amphipathic membrane active polyamine, antibody, drug product, hapten, digoxigenin, vitamin, biotin, fluorophore, antibody, monoclonal antibody, and antibody fragment.

In some embodiments, tetrapeptide modifying agents for reversibly attaching a first compound to an amine-containing second compound via a biologically labile tetrapeptide linker are described, the tetrapeptide modifying agents comprising:

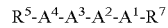

R$^5$-A$^4$-A$^3$-A$^2$-A$^1$-R$^7$     (formula V)

wherein

R$^5$ represents the first compound,

A$^4$ is a natural, non-natural isomeric, or synthetic hydrophobic L amino acid wherein the hydrophobicity index (Monera et al, J. Protein Sci. 1995, 1, 319) at pH 7 is 41 or greater, normalized to glycine, as it relates to the composition of the amino acid side chain (R-group), A$^3$ is an uncharged or basic hydrophilic L amino acid wherein the hydrophobicity index (Monera et al, J. Protein Sci. 1995, 1, 319) at pH 7 is −28 or less, normalized to glycine, as it relates to the composition of amino acid side chain (R-group), A$^2$ is a natural, non-natural isomeric, or synthetic hydrophobic L amino acid wherein the hydrophobicity index (Monera et al, J. Protein Sci. 1995, 1, 319) at pH 7 is 41 or greater, normalized to glycine, as it relates to the composition of the amino acid side chain (R-group), A$^1$ is L-proline, L-leucine, or L-N-methyl alanine, and R$^7$ comprises an amine-reactive group such as but not limited to: activated esters of TFP (tetrafluoro phenyl) or NHS (N-hydroxysuccinimide) 2-MT (2-mercaptothiazoline).

In some embodiments, A$^1$ is proline, A$^2$ and A$^4$ are independently alanine, valine, leucine, isoleucine or phenylalanine (side chains of —CH$_3$, —CH(CH$_3$)$_2$, —CH$_2$CH(CH$_3$)$_2$, —CH(CH$_3$)CH$_2$CH$_3$, or —CH$_2$C$_6$H$_5$, respectively), and A$^3$ is citrulline or asparagine (side chains of —(CH$_2$)$_3$NHCONH$_2$ or —CH$_2$CONH$_2$, respectively).

In some embodiments, A$^1$ is proline, A$^2$ and A$^4$ are phenylalanine, and A$^3$ is citrulline (FCitFP (SEQ ID NO: 12)). In some embodiments, A$^1$ is proline, A$^2$ is phenylalanine, A$^3$ is citrulline, and A$^4$ is alanine (ACitFP (SEQ ID NO: 3)).

In some embodiments, A$^1$ is L-proline, A$^2$ and A$^4$ are independently L-alanine, L-valine, L-leucine, L-isoleucine or L-phenylalanine (side chains of —CH$_3$, —CH(CH$_3$)$_2$, CH$_2$CH(CH$_3$)$_2$, —CH(CH$_3$)CH$_2$CH$_3$, or —CH$_2$C$_6$H$_6$, respectively), and A$^3$ is L-citrulline, L-asparagine, or L-lysine (side chains of —(CH$_2$)$_3$NHCONH$_2$, —CH$_2$CONH$_2$, or —(CH$_2$)$_4$NH$_3^+$, respectively).

In some embodiments, A$^1$ is L-proline, A$^2$ and A$^4$ are L-phenylalanine, and A$^3$ is L-citrulline (FCitFP (SEQ ID NO: 12)).

In some embodiments, A$^1$ is L-proline, A$^2$ is L-phenylalanine, A$^3$ is L-lysine, and A$^4$ is L-phenylalanine (FKFP (SEQ ID NO: 16)).

In some embodiments, A$^1$ is L-proline, A$^2$ is L-valine, A$^3$ is L-citrulline, and A$^4$ is L-phenylalanine (FCitVP (SEQ ID NO: 13)).

In some embodiments, A$^1$ is L-proline, A$^2$ is L-phenylalanine, A$^3$ is L-citrulline, and A$^4$ is L-valine (VCitFP (SEQ ID NO: 19)).

In some embodiments, A$^1$ is L-proline, A$^2$ is L-alanine, A$^3$ is L-citrulline, and A$^4$ is L-phenylalanine (FCitAP (SEQ ID NO: 8)).

In some embodiments, A$^1$ is L-proline, A$^2$ is L-phenylalanine, A$^3$ is L-citrulline, and A$^4$ is L-alanine (ACitFP (SEQ ID NO: 3)).

In some embodiments, A$^1$ is leucine, A$^2$ and A$^4$ are independently L-alanine, L-valine, L-leucine, L-isoleucine or L-phenylalanine (side chains of —CH$_3$, —CH(CH$_3$)$_2$, —CH$_2$CH(CH$_3$)$_2$, —CH(CH$_3$)CH$_2$CH$_3$, or —CH$_2$C$_6$H$_6$, respectively), and A³ is L-citrulline, L-asparagine, or L-lysine (side chains or —(CH₂)₃NHCONH₂, —CH₂CONH₂, of —(CH₂)₄NH₃⁺, respectively).

In some embodiments, A¹ is L-leucine, A² is L-phenylalanine, and A³ is L-lysine, and A⁴ is L-phenylalanine (FKFL (SEQ ID NO: 15)).

In some embodiments, A¹ is L-leucine, A² is L-phenylalanine, A³ is L-citrulline, and A⁴ is L-phenylalanine (FCitFL (SEQ ID NO: 11)).

In some embodiments, A¹ is L-N-methyl-alanine, A² and A⁴ are independently L-alanine, L-valine, L-leucine, L-isoleucine or L-phenylalanine (side chains of —CH₃, —CH(CH₃)₂, —CH₂CH(CH₃)₂, —CH(CH₃)CH₂CH₃, or —CH₂C₆H₆, respectively), and A³ is L-citrulline, L-asparagine, or L-lysine (side chains of —(CH₂)₃NHCONH₂, —CH₂CONH₂, or —(CH₂)₄NH₃⁺, respectively).

In some embodiments, A¹ is L-N-methyl-alanine, A² is L-phenylalanine, and A³ is L-citrulline, and A⁴ is L-phenylalanine (FCitF(Nme)A (SEQ ID NO: 9)).

In some embodiments, R₅ comprises a compound selected from the list comprising steric stabilizer, PEG, H—(CH₂)₀₋₂—(O—CH₂—CH₂)₁₋₅₀₀—O₀₋₁—(CH₂)₀₋₂—, PEG₁₋₁₀₀, targeting group, cell receptor ligand, integrin-binding ligand, RGD ligand, RGD mimic, asialoglycoprotein receptor (ASGPr) ligand, galactose, galactose derivative, N-acetylgalactosamine, folate, polynucleotide, polymer, polyamine, lipid, liposome, antibody, drug product, hapten, digoxigenin, vitamin, biotin, fluorophore, antibody, immunoglobulin, monoclonal antibody, and antibody fragment.

In some embodiments, a targeting group comprises a cell surface receptor ligand. A cell surface receptor can include, but is not limited to, asialoglycoprotein receptor and integrin receptor. An asialoglycoprotein receptor ligand can include, but is not limited to, galactose, galactosamine, N-formylgalactosamine, N-acetylgalactosamine, N-propionyl-galactosamine, N-n-butanoylgalactosamine, and N-iso-butanoylgalactosamine, or dimer, trimers or tetramers thereof. An integrin receptor can include, but is not limited to, an αvβ3 integrin and an αvβ6 integrin. An integrin receptor ligand can include, but is not limited to, an RGD or RGD mimic (see for example, US Patent Publication US-2015-0045573 A1, incorporated herein by reference).

A steric stabilizer can include, but is not limited to, a polyethylene glycol (PEG). A PEG contains 1-120 ethylene units, 3-30 ethylene units or 3-24 ethylene units.

In some embodiments, compounds for reversibly attaching a first compound to an amine-containing second compound via a biologically labile tetrapeptide linker are described, the compounds comprising the structure represented by:

(formula VI)

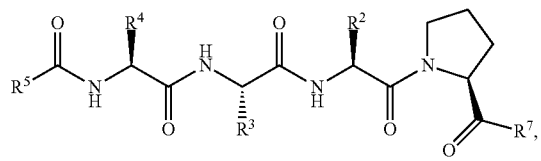

(formula VII)

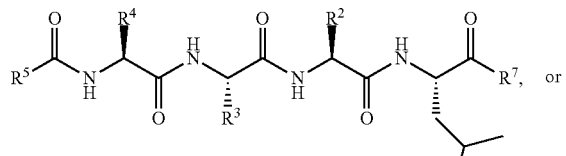

(formula VIII)

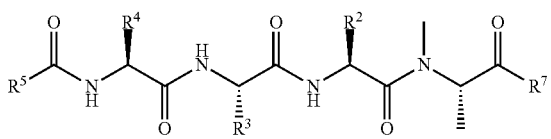

wherein
R⁵ represents the first compound,
R⁴ is an R-group (side chain) of a natural, non-natural isomeric, or synthetic hydrophobic L amino acid wherein the hydrophobicity index (Monera et al, J. Protein Sci. 1995, 1, 319) at pH 7 is 41 or greater, normalized to glycine, as it relates to the composition of the amino acid side chain (R-group)
R³ is an R-group (side chain) of a uncharged hydrophilic or basic hydrophilic L amino acid wherein the hydrophobicity index (Monera et al, J. Protein Sci. 1995, 1, 319) at pH 7 is −28 or less, normalized to glycine, as it relates to the composition of amino acid side chain (R-group), and
R² is an R group (side chain) of a natural, non-natural isomeric, or synthetic hydrophobic L amino acid wherein the hydrophobicity index (Monera et al, J. Protein Sci. 1995, 1, 319) at pH 7 is 41 or greater, normalized to glycine, as it relates to the composition of the amino acid side chain (R-group).
R⁷ comprises an amine-reactive group.
R⁷ is chosen such that reaction with an amine or amine-containing compound forms an amide bond with A¹. In some embodiments, amine-reactive group is TFP (tetrafluoro phenyl), or NHS (N-hydroxysuccinimide).

In some embodiments, R² and R⁴ are independently selected from the group consisting of: —CH₃, —CH(CH₃)₂, —CH₂CH(CH₃)₂, —CH(CH₃)CH₂CH₃, and —CH₂C₆H₅.

In some embodiments, R³ is selected from the group consisting of: —(CH₂)₃NHCONH₂ and —CH₂CONH₂.

In some embodiments, compounds for reversibly attaching a first compound to an amine-containing second compound via a biologically labile tetrapeptide linker are described, the compounds comprising the structure represented by:

(formula IX)

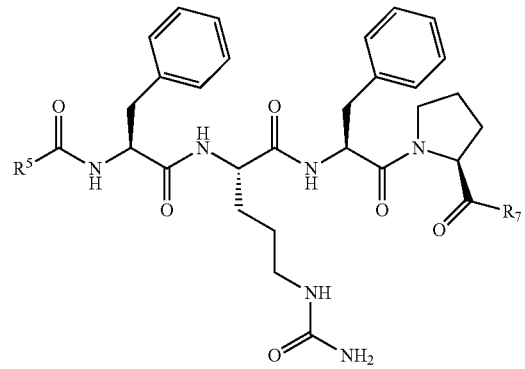

wherein R⁵ represents the first compound and R⁷ comprises an amine reactive group. R⁷ is chosen such that reaction with an amine or amine-containing compound forms an amide bond with A¹. In some embodiments, the amine-reactive group is TFP (tetrafluoro phenyl), or NHS (N-hydroxy succinimide).

In some embodiments, reversibly modified polyamines are described, a reversibly modified polyamine comprising:

  (formula X)

wherein
R⁵, A⁴, A³, A², and A¹ are each as described above,
P comprises a polyamine,
n is an integer greater than or equal to 1, and
each A¹ is linked to an amine on the polyamine via an amide bond.

In some embodiments, the polyamine is a membrane active polyamine. In some embodiments, the membrane active polyamine is an amphipathic membrane active polyamine.

In some embodiments, A¹ is L-proline, A² and A⁴ are independently L-alanine, L-valine, L-leucine, L-isoleucine or L-phenylalanine (side chains of —CH₃, —CH(CH₃)₂, CH₂CH(CH₃)₂, —CH(CH₃)CH₂CH₃, or —CH₂C₆H₆, respectively), and A³ is L-citrulline, L-asparagine, or L-lysine (side chains of —(CH₂)₃NHCONH₂, —CH₂CONH₂, or —(CH₂)₄NH₃⁺, respectively).

In some embodiments, A¹ is L-proline, A² and A⁴ are L-phenylalanine, and A³ is L-citrulline (FCitFP (SEQ ID NO: 12)).

In some embodiments, A¹ is L-proline, A² is L-phenylalanine, A³ is L-lysine, and A⁴ is L-phenylalanine (FKFP (SEQ ID NO: 16)).

In some embodiments, A¹ is L-proline, A² is L-valine, A³ is L-citrulline, and A⁴ is L-phenylalanine (FCitVP (SEQ ID NO: 13)).

In some embodiments, A¹ is L-proline, A² is L-phenylalanine, A³ is L-citrulline, and A⁴ is L-valine (VCitFP (SEQ ID NO: 19)).

In some embodiments, A¹ is L-proline, A² is L-alanine, A³ is L-citrulline, and A⁴ is L-phenylalanine (FCitAP (SEQ ID NO: 8)).

In some embodiments, A¹ is L-proline, A² is L-phenylalanine, A³ is L-citrulline, and A⁴ is L-alanine (ACitFP (SEQ ID NO: 3)).

In some embodiments, A¹ is leucine, A² and A⁴ are independently L-alanine, L-valine, L-leucine, L-isoleucine or L-phenylalanine (side chains of —CH₃, —CH(CH₃)₂, —CH₂CH(CH₃)₂, —CH(CH₃)CH₂CH₃, or —CH₂C₆H₆, respectively), and A³ is L-citrulline, L-asparagine, or L-lysine (side chains of —(CH₂)₃NHCONH₂, —CH₂CONH₂, or —(CH₂)₄NH₃⁺, respectively).

In some embodiments, A¹ is L-leucine, A² is L-phenylalanine, A³ is L-lysine, and A⁴ is L-phenylalanine (FKFL (SEQ ID NO: 15)).

In some embodiments, A¹ is L-leucine, A² is L-phenylalanine, A³ is L-citrulline, and A⁴ is L-phenylalanine (FCitFL (SEQ ID NO: 11)).

In some embodiments, A¹ is L-N-methyl-alanine, A² and A⁴ are independently L-alanine, L-valine, L-leucine, L-isoleucine or L-phenylalanine (side chains of —CH₃, —CH(CH₃)₂, CH₂CH(CH₃)₂, —CH(CH₃)CH₂CH₃, or —CH₂C₆H₆, respectively), and A³ is L-citrulline, L-asparagine, or L-lysine (side chains of —(CH₂)₃NHCONH₂, —CH₂CONH₂, or —(CH₂)₄NH₃⁺, respectively).

In some embodiments, A¹ is L-N-methyl-alanine, A² is L-phenylalanine, and A³ is L-citrulline, and A⁴ is L-phenylalanine (FCitF(Nme)A (SEQ ID NO: 9)).

In some embodiments, the reversibly modified polyamine is formed by reacting the polyamine with a plurality of described tetrapeptide modifying agents. In some embodiments, attachment of the tetrapeptide modifying agents to a membrane active polyamine masks membrane activity of the membrane active polyamine by forming a masked polyamine or delivery polymer.

In some embodiments, greater the 50% of the amines on the polyamine are modified (the value of n is greater than 50% of the number of amines on the polyamine). In some embodiments, greater the 60% of the amines on the polyamine are modified. In some embodiments, greater the 70% of the amines on the polyamine are modified. In some embodiments, greater the 75% of the amines on the polyamine are modified. In some embodiments, greater the 80% of the amines on the polyamine are modified. In some embodiments, greater the 85% of the amines on the polyamine are modified. In some embodiments, greater the 90% of the amines on the polyamine are modified. In some embodiments, greater the 95% of the amines on the polyamine are modified. In some embodiments, 100% of the amines on the polyamine are modified.

In some embodiments, R⁵ comprises a targeting group and the reversibly modified polyamine is further conjugated to an RNAi trigger. The RNAi trigger-reversibly modified polyamine conjugate can be used to deliver the RNAi trigger to cells in vivo for the purpose of knocking down target gene expression. The conjugate is formed and administered to a patient. Administration can be, but is not limited, to intravascular injection and subcutaneous injection. Cleavage (digestion) of the tetrapeptides by proteolytic enzymes in vitro or in vivo results in cleavage between A¹ and the polyamine to liberate the polyamine. The rate of release of the polyamine is sufficient to provide drug or RNAi trigger delivery.

In some embodiments, reversibly modified polyamines are described, a reversibly modified polyamine comprising:

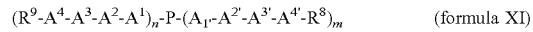  (formula XI)

wherein
A⁴, A³, A², and A¹ are each as described above,
A¹', A²', A³', and A⁴' are independently as described above for A¹, A², A³, and A⁴, respectively,
R⁹ comprises a targeting group,
R⁸ comprises a steric stabilizer
P comprises a polyamine,
n and m are each integers greater than or equal to 1, and
each A¹ and A¹' are linked to amines on the polyamine via amide bonds.

The reversibly modified polyamine is formed by reacting the polyamine with a plurality of described tetrapeptide modifying agents.

In some embodiments, the polyamine is a membrane active polyamine. In some embodiments, the membrane active polyamine is an amphipathic membrane active polyamine.

In some embodiments, greater the 50% of the amines on the polyamine are modified (the value of n+m is greater than 50% of the number of amines on the polyamine). In some embodiments, greater the 60% of the amines on the polyamine are modified. In some embodiments, greater the 70% of the amines on the polyamine are modified. In some embodiments, greater the 75% of the amines on the polyamine are modified. In some embodiments, greater the 80% of the amines on the polyamine are modified. In some embodiments, greater the 85% of the amines on the polyamine are modified. In some embodiments, greater the 90% of the amines on the polyamine are modified. In some embodiments, greater the 95% of the amines on the polyamine are modified. In some embodiments, 100% of the amines on the polyamine are modified.

In some embodiments, the reversibly modified polyamine is further conjugated to an RNAi trigger. The RNAi trigger-reversibly modified polyamine conjugate can be used to deliver the RNAi trigger to cells in vivo for the purpose of knocking down target gene expression. The conjugate is formed and administered to a patient. Administration can be, but is not limited to, intravascular injection and subcutaneous injection. Cleavage (digestion) of the tetrapeptides by proteolytic enzymes in vitro or in vivo results in cleavage between $A^1$ and the polyamine to liberate the polyamine. The rate of release of the polyamine is sufficient to provide drug or RNAi trigger delivery.

Surprisingly, we show that insertion of a C-terminal L-proline residue of a tetrapeptide linker greatly improves the cleavage characteristics of the linker. Regeneration of $H_2N—R^6$ ($H_2N—P$ from formulae X and XI) occurs at a significantly faster rate when L-proline is present at $A^1$. Without wishing to be bound by theory, endogenous enzymes appear to rapidly cleave the tetrapeptide between $A^3$ and $A^2$ to generate the first compound linked to an $A^4$-$A^3$ dipeptide ($R^5$-$A^4$-$A^3$-$CO_2H$) and the second compound linked to an $A^2$-$A^1$ dipeptide ($H_2N$-$A^2$-$A^1$-$N(H)$-$R^6$). The presence of proline at $A^1$ suppresses cleavage between $A^2$ and $A^1$. If several amino acids other than proline is present of position $A^1$, endogenous exoproteases appear to rapidly cleave $A^2$ from ($H_2N$-$A^2$-$A^1$-$N(H)$-$R^6$) to yield $H_2N$-$A^2$-$CO_2H$ plus $H_2N$-$A^1$-$N(H)$-$R^6$. Cleavage of the single amino acid from the second compound appears to be slow, resulting in slow regeneration of the original amine-containing compound ($H_2N$-$R^6$). In the absence of proline at position $A^1$, we observed that single amino acid conjugates ($H_2N$-$A^1$-$N(H)$-$R^2$) were readily formed, either by initial cleavage between $A^2$ and $A^1$ or by cleavage between $A^3$ and $A^2$ followed by cleavage between $A^2$ and $A^1$. In contrast, if proline, is present at position $A^1$, then the dipeptide $A^2$-$A^1$ appears to be rapidly cleaved by endogenous dipeptidases to yield $H_2N$-$A^2$-Pro-$CO_2H$ and the released second compound $H_2N—R^6$. Similar results are achieved with L-leucine or N-methyl alanine and position $A^1$.

As used herein, membrane active polyamines are surface active, amphipathic polymers that are able to induce one or more of the following effects upon a biological membrane: an alteration or disruption of the membrane that allows non-membrane permeable molecules to enter a cell or cross the membrane, pore formation in the membrane, fission of membranes, or disruption or dissolving of the membrane. As used herein, a membrane, or cell membrane, comprises a lipid bilayer. The alteration or disruption of the membrane can be functionally defined by the polymer's activity in at least one the following assays: red blood cell lysis (hemolysis), liposome leakage, liposome fusion, cell fusion, cell lysis, and endosomal release. Membrane active polymers that can cause lysis of cell membranes are also termed membrane lytic polymers. Polymers that preferentially cause disruption of endosomes or lysosomes over plasma membrane are considered endosomolytic. The effect of membrane active polymers on a cell membrane may be transient. Membrane active polymers possess affinity for the membrane and cause a denaturation or deformation of bilayer structures. Membrane active polymers may be synthetic or non-natural amphipathic polymers.

Delivery of a polynucleotide to a cell is mediated by the membrane active polymer disrupting or destabilizing the plasma membrane or an internal vesicle membrane (such as an endosome or lysosome), including by forming a pore in the membrane, or disrupting endosomal or lysosomal vesicles thereby permitting release of the contents of the vesicle into the cell cytoplasm.

As used herein, a steric stabilizer is a non-ionic hydrophilic polymer (either natural, synthetic, or non-natural) that prevents or inhibits intramolecular or intermolecular interactions of a molecule to which it is attached relative to the molecule containing no steric stabilizer. A steric stabilizer hinders a molecule to which it is attached from engaging in electrostatic interactions. Electrostatic interaction is the non-covalent association of two or more substances due to attractive forces between positive and negative charges. Steric stabilizers can inhibit interaction with blood components and therefore opsonization, phagocytosis, and uptake by the reticuloendothelial system. Steric stabilizers can thus increase circulation time of molecules to which they are attached. Steric stabilizers can also inhibit aggregation of a molecule. In some embodiments, a steric stabilizer is a polyethylene glycol (PEG) or PEG derivative. Suitable PEG molecules have about 1-120 ethylene glycol monomers.

Targeting groups (also targeting ligands) are used for targeting or delivery of a compound to target cells or tissues, or specific cells types. Targeting groups enhance the association of molecules with a target cell. Thus, targeting groups can enhance the pharmacokinetic or biodistribution properties of a conjugate to which they are attached to improve cellular distribution and cellular uptake of the conjugate. Binding of a targeting group, such as a ligand, to a cell or cell receptor may initiate endocytosis. Targeting groups may be selected from the group comprising: compounds with affinity to cell surface molecule, cell receptor ligands, and antibodies, antibody fragments, and antibody mimics with affinity to cell surface molecules. In some embodiments, the targeting group comprises a cell receptor ligand. A variety of ligands have been used to target drugs and genes to cells and to specific cellular receptors. Cell receptor ligands may be selected from the group comprising: carbohydrates, glycans, saccharides (including, but not limited to: galactose, galactose derivatives, mannose, and mannose derivatives), vitamins, folate, biotin, aptamers, peptides (including, but not limited to: RGD-containing, peptides, insulin, EGF, and transferrin, and RGD mimics).

As used herein, a ASGPr ligand (or ASGPr ligand) comprises a galactose and galactose derivative having affinity for the ASGPr equal to or greater than that of galactose. Binding of galactose targeting groups to the ASGPr(s) facilitates cell-specific targeting of the delivery peptide to hepatocytes and endocytosis of the delivery peptide into hepatocytes. ASGPr ligands may be selected from the group comprising: lactose, galactose, N-acetylgalactosamine (GalNAc), galactosamine, N-formylgalactosamine, N-acetyl-galactosamine, N-propionylgalactosamine, N-n-butanoylgalactosamine, and N-iso-butanoyl-galactosamine (Iobst, S. T. and Drickamer, K. *J.B.C.* 1996, 271, 6686). ASGPr ligands can be monomeric (e.g., having a single galactosamine) or multimeric (e.g., having multiple galactosamines).

RNAi triggers (also called dsRNAi triggers) inhibit gene expression through the biological process of RNA interference (RNAi). RNAi triggers comprise double stranded RNA or RNA-like structures typically containing 15-50 base pairs or 18-26 base pairs and having a nucleobase sequence at least 90% complementary over a core region to a coding sequence in an expressed target gene within the cell. RNAi triggers include, but are not limited to: short interfering RNAs (siRNAs), double-strand. RNAs (dsRNA), micro RNAs (miRNAs), short hairpin RNAs (shRNA), and dicer substrates (U.S. Pat. Nos. 8,084,599 8,349,809 and 8,513,207).

By inhibit, down-regulate, or knockdown gene expression, it is meant that the expression of the gene, as measured by the level of mRNA transcribed from the gene or the level of polypeptide, protein or protein subunit translated from the mRNA, is reduced below that observed in the absence of the blocking polynucleotide-conjugates described herein. Inhibition, down-regulation, or knockdown of gene expression, with a polynucleotide delivered by the compositions described herein, is below that level observed in the presence of a control inactive nucleic acid, a nucleic acid with scrambled sequence or with inactivating mismatches, or in absence of conjugation of the polynucleotide to the reversibly modified polymer.

In pharmacology and toxicology, a route of administration is the path by which a drug, fluid, poison, or other substance is brought into contact with the body. In general, methods of administering drugs and nucleic acids for treatment of a mammal are well known in the art and can be applied to administration of the compositions described herein. The compositions described herein can be administered via any suitable route, including parenterally, in a preparation appropriately tailored to that route. Thus, the compounds described herein can be administered by injection, for example, intravenously, intramuscularly, intracutaneously, subcutaneously, or intraperitoneally. Accordingly, the compositions described herein may be included in pharmaceutical compositions and/or may form part of a pharmaceutically acceptable carrier or excipient.

Parenteral routes of administration include intravascular (intravenous, intraarterial), intramuscular, intraparenchymal, intradermal, subdermal, subcutaneous, intratumor, intraperitoneal, intrathecal, subdural, epidural, and intralymphatic injections that use a syringe and a needle or catheter.

The described compositions are injected in pharmaceutically acceptable carrier solutions. Pharmaceutically acceptable refers to those properties and/or substances which are acceptable to the mammal from a pharmacological/toxicological point of view. The phrase pharmaceutically acceptable refers to molecular entities, compositions, and properties that are physiologically tolerable and do not typically produce an allergic or other untoward or toxic reaction when administered to a mammal. The term pharmaceutically acceptable means able to be approved by a regulatory agency of the Federal or a state government or listed in the U.S. Pharmacopeia or other generally recognized pharmacopeia for use in animals and more particularly in humans.

As used herein, a "pharmaceutical composition" comprises a pharmacologically effective amount of an Active Pharmaceutical Ingredient (API, also therapeutic product, e.g., RNAi trigger), a pharmaceutically acceptable carrier, and optionally one or more a pharmaceutically acceptable excipients. Pharmaceutically acceptable excipients (excipients) are substances other than the API that have been appropriately evaluated for safety and are intentionally included in the drug delivery system. Excipients do not exert or are not intended to exert a therapeutic effect at the intended dosage. Excipients may act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use.

Excipients include, but are not limited to: absorption enhancers, anti-adherents, anti-foaming agents, anti-oxidants, binders, binders, buffering agents, carriers, coating agents, colors, delivery enhancers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents. A pharmaceutically acceptable excipient may or may not be an inert substance.

The pharmaceutical compositions described herein can contain other additional components commonly found in pharmaceutical compositions. The pharmaceutically-active materials may include, but are not limited to: anti-pruritics, astringents, local anesthetics, or anti-inflammatory agents (e.g., antihistamine, diphenhydramine, etc.). It is also envisaged that cells, tissues or isolated organs that express or comprise the herein defined RNAi triggers may be used as "pharmaceutical compositions". As used herein, "pharmacologically effective amount," "therapeutically effective amount," or simply "effective amount" refers to that amount of an RNAi trigger to produce the intended pharmacological, therapeutic or preventive result.

Medicaments containing a tetrapeptide linker are also an object of the present invention, as are processes for the manufacture of such medicaments, which processes comprise bringing one or more compounds containing a tetrapeptide linker, and, if desired, one or more other therapeutically valuable substances into a galenical administration form.

EXAMPLES

Example 1

Synthesis of Tetrapeptide Linkers and Conjugates Having Tetrapeptide Linkers.

A) Synthesis of Peptide and AENA Labeled Peptides.

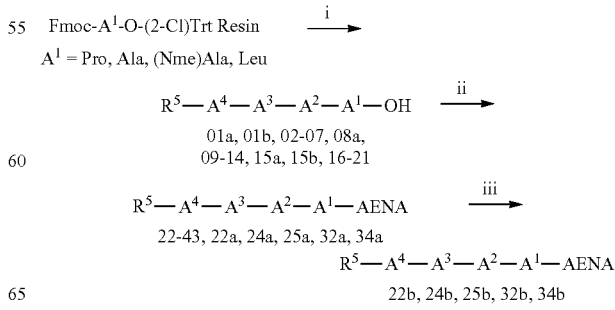

(i) Solid Phase Synthesis of Compounds 1-21:

Peptide acids were synthesized from commercially available 2-Cl-Trt resin (EMD Millipore, Billerica, Mass.) preloaded with proline, leucine, alanine or N-methyl Alanine. Stepwise addition was performed using standard methods in the art of solid phase synthesis. Coupling was performed using PYBOP (4 eq), amino acid (4 eq), and DIEA (8 eq). Fmoc deprotection was performed with 20% piperdine in DMF.

After peptide synthesis the N-terminal amino acid was deprotected and coupled with the indicated $R^5$ group. Coupling was performed using 2 eq of NHS activated esters of either NAG(OAc)$_3$ (as prepared in U.S. Pat. No. 8,802,773 and Rozema et al. 2015) or PEG$_{12}$ (Quanta Biodesign, Plain City, Ohio, CAS #: 756525-94-7) in DMF containing 4 eq of DIEA. Other $R^5$ groups can be attached using similar syntheses. Following attachment of $R^5$ the peptides were cleaved from resin using HFIP (30%) in DCM for 0.25 hours. After solvent removal the residue was triturated with Et$_2$O. Substrates were subsequently used without further purification.

(ii) General Preparation of Compounds 22-43 (22a, 24a, 25a, 32a, 34a):

To a solution of crude peptide substrate (1-21) was added PyBOP (2 eq), DIEA (2 ea), then AENA (2 eq) and stirred for 1 h at room temp. Upon completion solvent was removed in vacuo. Compounds 24a, 25a, 32a, and 34a were subsequently used without further purification. All other substrates were purified using HPLC with a Thermo Scientific Aquasil C18 reverse-phase column (250×21.2, Waltham, Mass.) eluting a gradient of acetonitrile and water buffered with 0.1% formic acid. After purification all compounds were dried by lyophilization.

(iii) Preparation of Compounds 22b, 24b, 25b, 32b and 34b:

Compounds 24a and 25a were treated with 2% Hydrazine in DMF for 15 min and all solvents were subsequently removed in vacuo. Compound 32a was treated with 50% TFA in DCM for 1 h and all solvents were subsequently removed in vacuo. Compound 34a was treated with neat formic acid for 18 h and all solvents were subsequently removed in vacuo. A portion of unpurified compound 22a was treated with MeOH (25%), H$_2$O (45%), and TEA (35%), stirred at room temp. overnight, and all solvents were subsequently removed in vacuo. All compounds, de-protected as described, were subsequently purified by HPLC as described in step (ii).

B. General Preparation of Compounds 44a, 44b, 45a, 45b and 34b, Ester Activation of Peptide Substrates (iv):

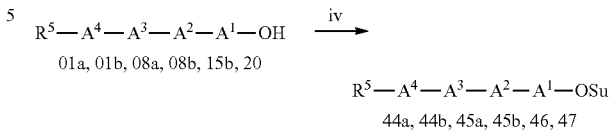

Crude compounds 01a, 01b, 08a, 08b, 15b, and 20 were first purified on HPLC as described in step (ii). Prior to purification by HPLC compounds 01a and 08a were treated with MeOH (25%), H$_2$O (45%), and TEA (35%) as in the preparation of 22b described in step (iii). Subsequently all compounds were activated as follows. In a flame dried flask, to a solution at 0° C., containing the purified substrate in DMF or DCM at 0.2 M concentration was added NHS (3 eq) and DCC (3 eq) and allowed to stir at room temperature under argon overnight. Upon completion the mixture was partially concentrated, chilled to −20° C., filtered and then all solvents were removed in vacuo. The residue was dissolved in a minimum of DCM and MeOH, precipitated into cold Et$_2$O and collected by decantation of the solvent after centrifugation. Precipitation into Et$_2$O was repeated until no residual dicyclohexylurea was detectable as confirmed by NMR. All prepared compounds were subsequently used without further purification.

C) Synthesis of EDANS Labeled Substrates, General Preparation of Compounds 48-59:

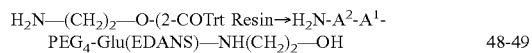

Each peptide acid was synthesized from commercially available 2-Cl-Trt resin (EMD Millipore, Billerica, Mass.) pre-loaded with ethanol amine. Stepwise solid phase synthesis was performed as described in step (i). After peptide synthesis the N-terminal FMOC was removed and the sequence cleaved from resin using 5% TFA, 5% H$_2$O in DCM for 0.5 hours and purified by HPLC as described in step (ii). Prior to purification compounds 52 and 53 were treated with 50% TFA, 5% TIS, 5% H$_2$O in DCM for 1 hour.

D) Preparation of Compound 60 (vi), Synthesis of Control for Digestion Assay:

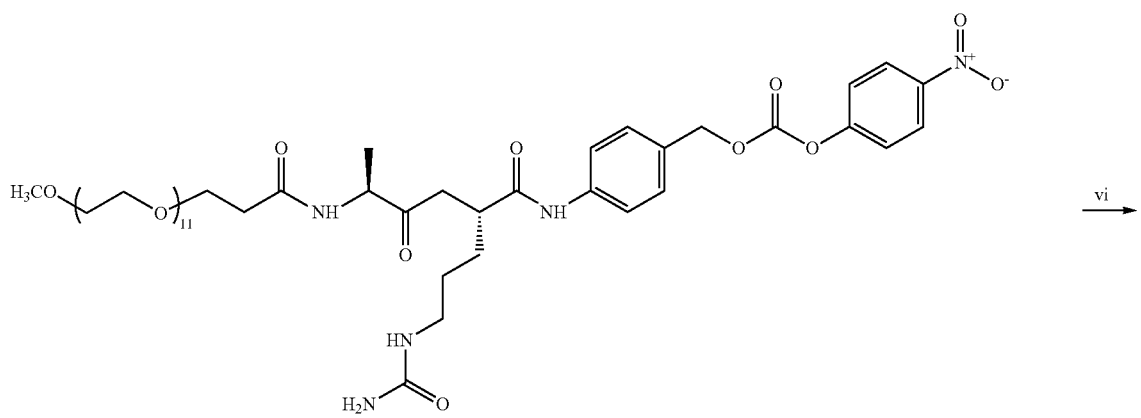

PEG$_{12}$-ACit-PABC-PNP

-continued

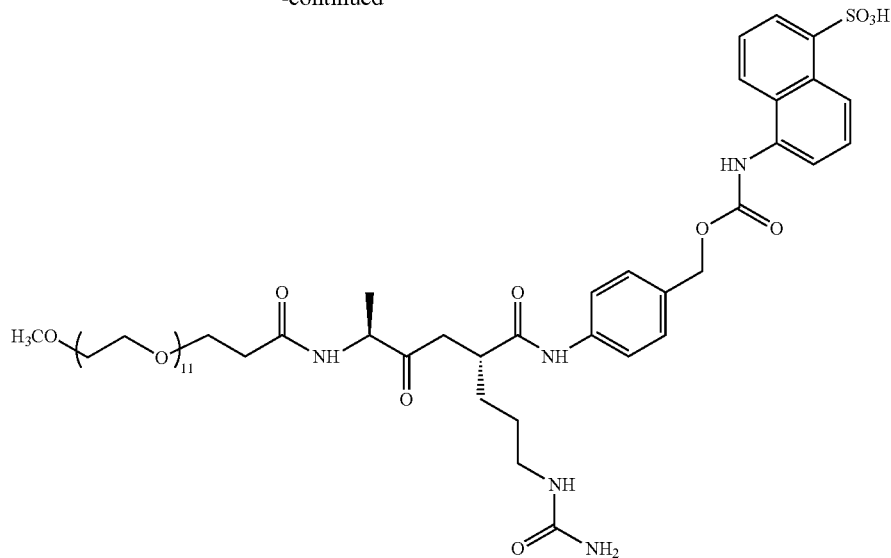

60

To a solution containing PEG$_{12}$-ACit-PABC-PNP (0.052 mmol, 56 mg), prepared as previously described (U.S. Pat. No. 8,802,733, Rozema et al. 2015, Carlson et al. 2015), and TEA (0.078 mmol, 10.8 μL) in DMF (400 uL) was added EDANS (0.052 mmol, 14 mg) and let to stir as a suspension at room temperature under argon overnight. Upon completion all solvents were removed in vacuo, the crude residue was triturated with Et$_2$O and purified using Sift eluting a gradient of MeOH (10-20%) in CHCl$_3$. Yield 58 mg (92%).

TABLE 1

Peptide Linkers.

| Compound | R$^5$ | A$^4$ | A$^3$ | A$^2$ | A$^1$ | *R$^6$ |
|---|---|---|---|---|---|---|
| 01a | NAG(OAc)$_3$ | Phe | Cit | Phe | Pro | OH |
| 01b | PEG$_{12}$ | Phe | Cit | Phe | Pro | OH |
| 02 | PEG$_{12}$ | Phe | Lys(dde) | Phe | Pro | OH |
| 03 | PEG$_{12}$ | Phe | Lys(dde) | Phe | Leu | OH |
| 04 | NAG(OAc)$_3$ | Phe | Cit | Val | Pro | OH |
| 05 | PEG$_{12}$ | Phe | Cit | Phe | Leu | OH |
| 06 | NAG(OAc)$_3$ | Val | Cit | Phe | Pro | OH |
| 07 | PEG$_{12}$ | Phe | Cit | Phe | (Nme)Ala | OH |
| 08a | NAG(OAc)$_3$ | Phe | Cit | Ala | Pro | OH |
| 08b | PEG$_{12}$ | Phe | Cit | Ala | Pro | OH |
| 09 | PEG$_{12}$ | Ala | Cit | Phe | Pro | OH |
| 10 | PEG$_{12}$ | Phe | Asn(dmcp) | Phe | Pro | OH |
| 11 | NAG(OAc)$_3$ | Phe | Cit | Ala | Ala | OH |
| 12 | PEG$_{12}$ | Phe | Asp(O$^t$Bu) | Phe | Pro | OH |
| 13 | NAG(OAc)$_3$ | Ala | Cit | Ala | Ala | OH |
| 14 | NAG(OAc)$_3$ | Cit | Ala | Ala | Ala | OH |
| 15a | NAG(OAc)$_3$ | Ala | Cit | Ala | Pro | OH |
| 15b | PEG$_{12}$ | Ala | Cit | Ala | Pro | OH |
| 16 | PEG$_{12}$ | Gly | Phe | Leu | Gly | OH |
| 17 | NAG(OAc)$_3$ | Phe | Cit | Phe | Ala | OH |
| 18 | NAG(OAc)$_3$ | — | Cit | Ala | Ala | OH |
| 19 | NAG(OAc)$_3$ | — | Ala | Ala | Ala | OH |
| 20 | PEG$_{12}$ | — | Cit | Ala | Pro | OH |
| 21 | NAG(OAc)$_3$ | — | Ala | Cit | Ala | OH |
| 22a | NAG(OAc)$_3$ | Phe | Cit | Phe | Pro | AENA |
| 22b | NAG(OH)$_3$ | Phe | Cit | Phe | Pro | AENA |
| 23 | PEG$_{12}$ | Phe | Cit | Phe | Pro | AENA |
| 24a | PEG$_{12}$ | Phe | Lys(dde) | Phe | Pro | AENA |
| 24b | PEG$_{12}$ | Phe | Lys(NH$_2$) | Phe | Pro | AENA |
| 25a | PEG$_{12}$ | Phe | Lys(dde) | Phe | Leu | AENA |
| 25b | PEG$_{12}$ | Phe | Lys(NH$_2$) | Phe | Leu | AENA |
| 26 | NAG(OAc)$_3$ | Phe | Cit | Val | Pro | AENA |
| 27 | PEG$_{12}$ | Phe | Cit | Phe | Leu | AENA |
| 28 | NAG(OAc)$_3$ | Val | Cit | Phe | Pro | AENA |
| 29 | PEG$_{12}$ | Phe | Cit | Phe | (Nme)Ala | AENA |
| 30 | NAG(OAc)$_3$ | Phe | Cit | Ala | Pro | AENA |

TABLE 1-continued

Peptide Linkers.

| Compound | $R^5$ | $A^4$ | $A^3$ | $A^2$ | $A^1$ | *$R^6$ |
|---|---|---|---|---|---|---|
| 31 | $PEG_{12}$ | Ala | Cit | Phe | Pro | AENA |
| 32a | $PEG_{12}$ | Phe | Asn(dmcp) | Phe | Pro | AENA |
| 32b | $PEG_{12}$ | Phe | Asn($NH_2$) | Phe | Pro | AENA |
| 33 | $NAG(OAc)_3$ | Phe | Cit | Ala | Ala | AENA |
| 34a | $PEG_{12}$ | Phe | Asp($O^tBu$) | Phe | Pro | AENA |
| 34b | $PEG_{12}$ | Phe | Asp(OH) | Phe | Pro | AENA |
| 35 | $NAG(OAc)_3$ | Ala | Cit | Ala | Ala | AENA |
| 36 | $NAG(OAc)_3$ | Cit | Ala | Ala | Ala | AENA |
| 37 | $NAG(OAc)_3$ | Ala | Cit | Ala | Pro | AENA |
| 38 | $PEG_{12}$ | Gly | Phe | Leu | Gly | AENA |
| 39 | $NAG(OAc)_3$ | Phe | Cit | Phe | Ala | AENA |
| 40 | $NAG(OAc)_3$ | — | Cit | Ala | Ala | AENA |
| 41 | $NAG(OAc)_3$ | — | Ala | Ala | Ala | AENA |
| 42 | $PEG_{12}$ | — | Cit | Ala | Pro | AENA |
| 43 | $NAG(OAc)_3$ | — | Ala | Cit | Ala | AENA |
| 44a | $NAG(OH)_3$ | Phe | Cit | Phe | Pro | OSu |
| 44b | $PEG_{12}$ | Phe | Cit | Phe | Pro | OSu |
| 45a | $NAG(OH)_3$ | Phe | Cit | Ala | Pro | OSu |
| 45b | $PEG_{12}$ | Phe | Cit | Ala | Pro | OSu |
| 46 | $PEG_{12}$ | Ala | Cit | Ala | Pro | OSu |
| 47 | $PEG_{12}$ | — | Cit | Ala | Pro | OSu |
| 48 | $H_2N$ | — | — | Phe | Pro | PGA |
| 49 | $H_2N$ | — | — | Leu | Pro | PGA |
| 50 | $H_2N$ | — | — | Val | Pro | PGA |
| 51 | $H_2N$ | — | — | Phe | (Nme)Ala | PGA |
| 52 | $H_2N$ | — | — | Asn($NH_2$) | Pro | PGA |
| 53 | $H_2N$ | — | — | Ser(OH) | Pro | PGA |
| 54 | $H_2N$ | — | — | Phe | Leu | PGA |
| 55 | $H_2N$ | — | — | Ala | Pro | PGA |
| 56 | $H_2N$ | — | — | Phe | Ala | PGA |
| 57 | $H_2N$ | — | — | — | Leu | PGA |
| 58 | $H_2N$ | — | — | Gly | Pro | PGA |
| 59 | $H_2N$ | — | — | — | Ala | PGA |
| 60 | $PEG_{12}$ | — | Ala | Cit | PABC | EDANS |

*where R6 = —OH, $A^1$ terminates in a carboxyl group (i.e., —OH replaces —NH—)

Structures for some components are shown in FIG. 1.

Example 2

Rate of Cleavage of Tetrapeptide Linkers.

Various amino acid combinations, tetrapeptides, were used to link various first moieties ($R^5$) and an AENA report group second compound ($R^6$) to form assay substrates (substrates). Cleavage rate of the peptides were evaluated by analysis of digestion of the substrates in the presence of rat lysosomal extract.

Reporting groups were coupled to the C-terminus of the peptide substrates as described above for UV-vis monitoring to explore the influence of amino acid sequence on kinetics of peptide degradation by HPLC. N-(2-aminoethyl)-4-nitroaniline (AENA) or N-(aminoethyl)-5-napthylamine-1-sulfonic acid (EDANS) were used as reporting groups for HPLC monitoring as neither absorptivity nor lambda maximum were affected for either after cleavage from the peptide. The N-terminus of each peptide substrate was modified with either methoxy polyethylene glycol ($PEG_{12}$) or N-acetyl galactosamine ($NAG(OR)_3$) (FIG. 1).

Digestion Assay:

Proteolytic digestion experiments were carried out at a fixed substrate concentration (0.51 μmol) using liver lysosomal (enzyme) extract (0.45 μg/μL) in a 25 mM MES solution buffered to pH 5 containing 1% CHAPS and 1.8 mM DTT incubated at 37° C. Enzyme extract was activated in the presence of DTT for 15 minutes at 37° C. prior to addition of AENA labeled peptide substrates. At various time points, up to 26 h, 20 μL aliquots were removed and acidified to a pH of 3 with TFA. Analysis of fractions was performed using HPLC with a Aquasil C18 reverse-phase column (250×4.6, Thermofisher, Waltham, Mass.), monitored at 390 nm and 335 nm for AENA and EDANS respectively. Elution was performed with a gradient of acetonitrile and water buffered with 0.1% formic acid. Generation of unmodified reporter molecule was measured. To minimize freeze thaw cycles the lysosomal extract was dispensed into multiple aliquots prior to storage at −80° C. A new aliquot was employed for each study and used immediately upon thawing. Lysosomal extract was sourced from female Hans Wistar rats by differential density gradient centrifugation (Graham et al. 2000). Protein concentration of lysosomal extract was determined by standard BCA protein assay protocols. Compound 60 was used for normalization of velocity between experiments (Tables 2-4). The average experimental velocity observed for 60 over multiple assays was 123.8 nmol/h. Normalized sample velocity was calculated as: [(average compound 60 velocity±experimental compound 60 velocity)]×sample experimental velocity.

Rate (also called velocity of degradation or velocity) was extrapolated during early linear turnover (Table 2). As used herein, rate is defined as the linear rate of reporting group generation at less than 50% completion (digestion rate was assumed to be linear at less than 50% completion). For substrates in which cleavage deviated from consecutive first order kinetics, the percent of reporting group liberated at the endpoint of digestion was used as a metric for comparison.

The date in Table 2 indicate that fastest rates of cleavage were observed with tetrapeptides having bulky hydrophobic amino acids and positions $A^2$ and $A^4$, bulky hydrophilic (polar) amino acids at position $A^3$, and proline or leucine at position $A^1$. In some embodiments, the amino acid at position $A^1$ is proline.

Tetrapeptide linkers having proline at the $A^1$ position had the highest velocities. If the proline of compounds 30 (FCitAP (SEQ ID NO: 8)), and 23 (FCitFP (SEQ ID NO: 12)) was changed to alanine, compounds 33 (FCitAA (SEQ ID NO: 7)) and 39 (FCitFA (SEQ ID NO: 10)), a dramatic reduction in rate and time to completion of digestion was observed. Substituting leucine at $A^1$ in compound 27 with proline, as shown in compound 23, resulted in a considerable increase in velocity for the proline-containing tretrapeptide. A small increase in velocity was also observed the proline-containing compound 24b compared to the when leucine-containing compound 25b.

Tetrapeptides having larger (bulky) hydrophobic amino acids at positions $A^2$ and $A^4$ also generally exhibited higher velocities. Increasing side chain bulk at the $A^2$ position, compounds 30, 26 and 23, increased velocity of digestion. Similarly, increasing side chain bulk at the $A^4$ position increased velocity of digestion, as shown in compounds 31, 28 and 23, respectively.

Tetrapeptides having bulky polar (neutral or positively charged) amino acids at position $A^3$ exhibited faster rates of cleavage, see compounds 23, 24b, 32b, and 34b.

Figure 2:
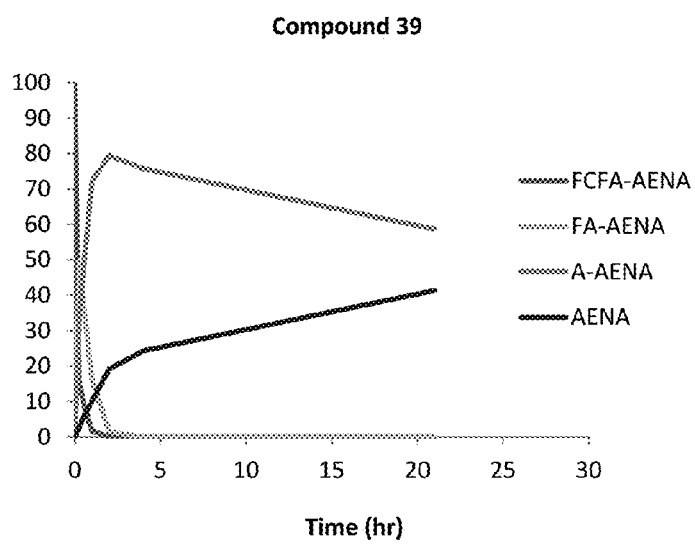
FIG. 2. Graph illustrating: A) Rate of digestion for compound 39, and B) Rate of digestion for compound 29.
Figure 2:
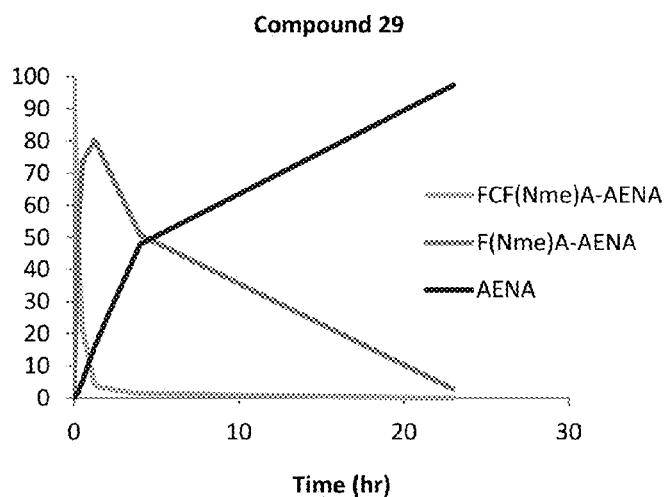
Figure 3:
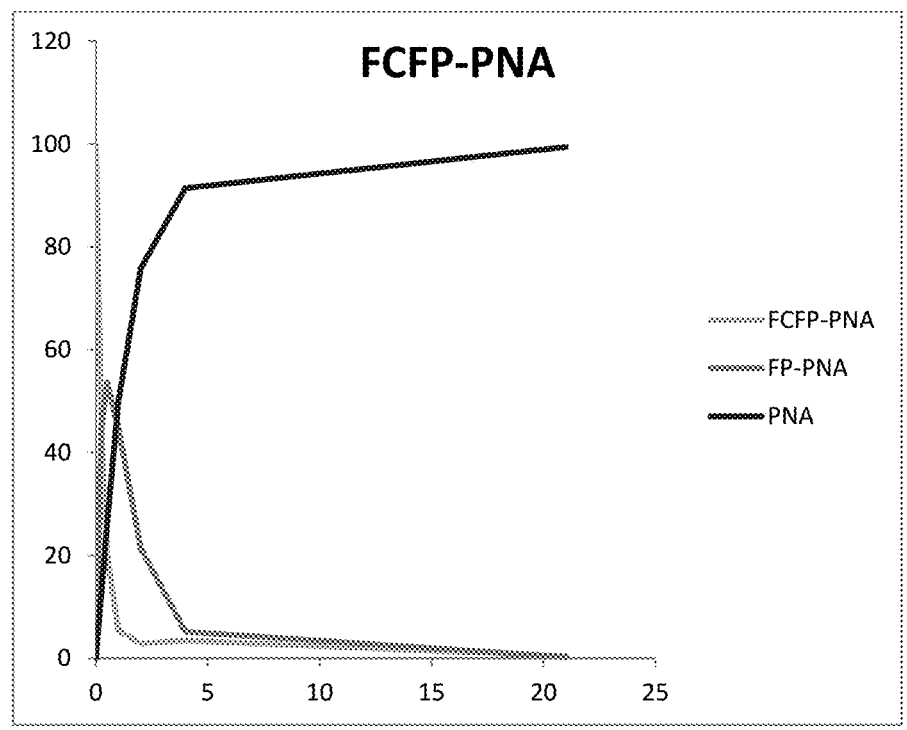
FIG. 3. Graph illustrating reaction kinetics for compounds 29 and 39, rates of intermediates generated (%) over time (hr) (C=citrulline).

N-methylation of compound 39 at $A^1$, to yield compound 29, resulted in a faster rate and faster completion of digestion (see also FIG. 2).

TABLE 3

Cleavage velocity of FCitFP (SEQ ID NO: 12) linker having various N-terminal ($R^5$) (compounds 23, 22a, and 22b).

| Assay substrate | Velocity nmol/h | | |
|---|---|---|---|
| | compound 60 | Sample | Normalized |
| (23) $PEG_{12}$-FCitFP-AENA | 123.6 | 192.7 | 192.9 |
| (22a) NAG(OAc)$_3$-FCitFP-AENA | 144.0 | 244.9 | 210.5 |
| (22b) NAG(OH)$_3$-FCitFP-AENA | 137.8 | 223.7 | 201.0 |

Example 3

Effect of Amino Acids $A^1$ and $A^2$ on Rate of Digestion of Dipeptides.

Dipeptide substrates having amine termini and a C-terminal ($R^6$) EDANS reporters, were made to further analyze the effects of amino acids $A^1$ and $A^2$ on cleavage rate. The dipeptides substrates mimic the tetrapeptide linkers following a first cleavage event of the tetrapeptide between amino acids $A^2$ and $A^3$. The dipeptides were treated with extracts and digestion products were analyzed as described above. As seen in Table 4, dipeptides having a proline at $A^1$ exhibited the fasted cleavage rate. In agreement with the data in Table 2, cleavage rate was found to be dependent on the amino acid at position $A^1$ and the size and charge of the amino acid as position $A^2$ (Table 4). Peptides with proline at

TABLE 2

Cleavage velocity of various peptide linkers. Various peptides were synthesized and cleavage velocity was determined.

| Assay Substrate | Peptide Sequence | SEQ ID NO: | (60) Velocity nmol/hr | Sample Velocity nmol/hr | Normalized Velocity nmol/hr | % Released at Endpoint (21 hr) |
|---|---|---|---|---|---|---|
| (23) $PEG_{12}$-FCitFP-AENA | FCitFP | 12 | 123.6 | 192.7 | 192.9 | *99.5 |
| (24b) $PEG_{12}$-FKFP- AENA | FKFP | 16 | 134.7 | 134.8 | 123.9 | ***98.9 |
| (25b) $PEG_{12}$-FKFL- AENA | FKFL | 15 | 123.5 | 117.0 | 117.4 | **99.8 |
| (26) NAG(OAc)$_3$-FCitVP- AENA | FCitVP | 13 | 144.3 | 119.5 | 102.5 | 97.8 |
| (27) $PEG_{12}$-FCitFL- AENA | FCitFL | 11 | 123.5 | 94.5 | 94.7 | **99.7 |
| (28) NAG(OAc)$_3$-VCitFP- AENA | VCitFP | 19 | 137.8 | 84.3 | 75.8 | *99.4 |
| (29) $PEG_{12}$-FCitF(Nme)A- AENA | FCitF(Nme)A | 9 | 123.6 | 62.5 | 62.6 | *97.3 |
| (30) NAG(OAc)$_3$-FCitAP- AENA | FCitAP | 8 | 108.4 | 54.3 | 62.0 | 96.5 |
| (31) $PEG_{12}$-ACitFP- AENA | ACitFP | 3 | 123.6 | 49.5 | 49.6 | *98.9 |
| (32b) $PEG_{12}$-FNFP- AENA | FNFP | 17 | 134.7 | 42.0 | 38.6 | ***99.3 |
| (33) NAG(OH)$_3$-FCitAA- AENA | FCitAA | 7 | 137.8 | — | — | 68.5 |
| (34b) $PEG_{12}$-FDFP- AENA | FDFP | 14 | 134.7 | 18.0 | 16.6 | ***66.5 |
| (35) NAG(OAc)$_3$-ACitAA- AENA | ACitAA | 1 | 120.0 | — | — | 49.8 |
| (36) NAG(OAc)$_3$-CitAAA- AENA | CitAAA | 5 | 100.9 | — | — | **47.7 |
| (37) NAG(OAc)$_3$-ACitAP- AENA | ACitAP | 2 | 108.0 | 11.8 | 13.5 | 44.2 |
| (38) $PEG_{12}$-GFLG- AENA | GFLG | 18 | 127.4 | 10.0 | 9.7 | **47.8 |
| (39) NAG(OAc)$_3$-FCitFA- AENA | FCitFA | 10 | 108.4 | — | — | 40.5 |
| (40) NAG(OAc)$_3$-CitAA- AENA | CitAA | | 120.0 | 3.7 | 3.9 | 15.6 |
| (41) NAG(OAc)$_3$-AAA- AENA | AAA | | 120.0 | 1.6 | 1.6 | 8.2 |
| (42) $PEG_{12}$-CitAP- AENA | CitAP | | 135.2 | 1.0 | 0.9 | **5.8 |
| (43) NAG(OAc)$_3$-ACA- AENA | ACitA | | 120.0 | — | — | 1.1 |

*Endpoint at 23 hours
**Endpoint at 24 hours
***Endpoint at 26 hours.
(compound numbers and amino acids are in bold)

For a given tetrapeptide, rate of cleavage (rate of liberation of unmodified $H^2N$—$R^6$) was not significantly affected by the identity of compound $R^5$. Compounds 22a and 23 were essentially equivalent in terms of rate of proteolytic digestion (Table 3). Similarly it was shown that acetyl modified NAG(OAc)$_3$, compound 22a, had a negligible effect on the velocity of digestion when compared to the unmodified analog, compound 22b (Table 3).

position $A^1$ has the greatest rate of cleavage. Rate of cleavage also increased with increasing size and hydrophobicity of the $A^2$ amino acid, as seen for compounds 48, 49, 50, 52, 55 and 58.

Addition of phenylalanine to compounds 57 and 59 (to yield compounds 54 and 56, respectively) resulted in a substantial increase in the velocity of digestion despite the additional amino acid.

TABLE 4

Cleavage velocity of dipeptide EDANS C-terminal modified substrates.

| Compound Name | Substrate Sequence | (60) Velocity nmol/hr | Sample Velocity nmol/hr | Normalized Velocity nmol/hr |
|---|---|---|---|---|
| (48) $H_2N$-FP-PEG$_4$-Glu(EDANS)-NH-(CH$_2$)$_2$-OH | F-P | 145.0 | 448.5 | 383.0 |
| (49) $H_2N$-LP-PEG$_4$-Glu(EDANS)-NH-(CH$_2$)$_2$-OH | L-P | 127.6 | 349.1 | 338.7 |
| (50) $H_2N$-VP-PEG$_4$-Glu(EDANS)-NH-(CH$_2$)$_2$-OH | V-P | 135.2 | 213.5 | 195.5 |
| (51) $H_2N$-F(Nme)A-Glu(EDANS)-NH-(CH$_2$)$_2$-OH | F-(Nme)A | 135.2 | 177.6 | 162.6 |
| (52) $H_2N$-NP-PEG$_4$-Glu(EDANS)-NH-(CH$_2$)$_2$-OH | N-P | 127.6 | 156.5 | 151.9 |
| (53) $H_2N$-SP-PEG$_4$-Glu(EDANS)-NH-(CH$_2$)$_2$-OH | S-P | 127.6 | 145.0 | 140.7 |
| (54) $H_2N$-FL-PEG$_4$-Glu(EDANS)-NH-(CH$_2$)$_2$-OH | F-L | 145.0 | 155.0 | 132.4 |
| (55) $H_2N$-AP-PEG$_4$-Glu(EDANS)-NH-(CH$_2$)$_2$-OH | A-P | 135.2 | 125.7 | 115.1 |
| (56) $H_2N$-FA-PEG$_4$-Glu(EDANS)-NH-(CH$_2$)$_2$-OH | F-A | 135.2 | 61.3 | 56.1 |
| (57) $H_2N$-L-PEG$_4$-Glu(EDANS)-NH-(CH$_2$)$_2$-OH | L | 135.2 | 58.5 | 53.3 |
| (58) $H_2N$-GP-PEG$_4$-Glu(EDANS)-NH-(CH$_2$)$_2$-OH | G-P | 127.6 | 14.4 | 13.9 |
| (59) $H_2N$-A-PEG$_4$-Glu(EDANS)-NH-(CH$_2$)$_2$-OH | A | 135.2 | 7.9 | 7.2 |

Example 4

Analysis of Digestion Using Extracts from Different Sources.

The observed rates of cleavage were not dependent on the source of proteolytic enzymes. The order of increasing velocity (23>30>37>42) was maintained when digested using commercially available rat and human liver S9 extract (Xenotech LLC, Lenexa, Kans.) (Table 5). Thus rates of cleavage are expected to be similar across different species and cell types.

TABLE 5

Relative velocity of substrates in different extracts.

| Compound Name | Substrate Sequence (SEQ ID NO:) | Lysosomal Extract | RAT S9 Extract | HUMAN S9 Extract |
|---|---|---|---|---|
| (23) PEG$_{12}$-FCFP-AENA | FCitFP (12) | 100.0 | 100.0 | 100.0 |
| (30) NAG(OAc)$_3$-FCitAP-AENA | FCitAP (8) | 32.1 | 28.3 | 45.7 |
| (37) NAG(OAc)$_3$-ACitAP-AENA | ACitAP (2) | 7.0 | 3.3 | 7.1 |
| (42) PEG$_{12}$-CitAP-AENA | CitAP | 0.5 | 0.6 | 1.7 |

*Normalized to compound 23.

Example 5

Analysis of Peptide Linker Digestion Intermediates.

Aliquots from examples 2 and 3 were further analyzed by HPLC and electro-spray ionization mass spectrometry to identify digestion intermediates. The analysis indicated multiple scissile locations for the initial endoproteolytic event of substrate degradation. Tetrapeptide linkers having a proline at position $A^1$ (22a, 22b, 23, 24b, 26, 28, 30, 31, 34b, 37, and 42) did not appear to generate a significant amount of $H_2N$-Pro-$R^6$ intermediate, i.e. there did not appear to be significant digestion between proline at $A^1$ and the amino acid at position $A^2$. Only $A^2$-Proline-AENA or free AENA was observed. When $A^1$ was alanine or leucine, the rate limiting step was proteolysis of the final residue. Digestion intermediates are shown for Compounds 39 (FCitFA (SEQ ID NO: 10)) and 29 (FCitF(Nme)A (SEQ ID NO: 9)) in FIG. 2.

Example 6

Release of $H_2N$—$R^6$ was not Impaired by Steric Bulk of a Polymeric Compound at $R^6$.

PEG tetrapeptide modifying agents were synthesized by using a PEG group at $R^5$ and an activated ester at $R^7$ (formula V). Membrane active polyamines (see below) were modified with Factor VII siRNA, CDM-NAG and the indicated tetrapeptide (45b, 46) or tripeptide control (47) modifying agents as previously described (U.S. Pat. Nos. 8,137,695 and 8,426,554) to form a dynamic polyconjugate delivery polymer. 1 mg/kg polymer conjugated to 0.25 mg/kg siRNA was then injected into mice. At day 5, samples were collected and assayed for Factor VII. Knockdown of Factor VII requires cleavage of the modifying agent from the polyamine at a rate similar to the previously described CDM masking agents and dipeptide-PABC masking agents. As shown in Table 6, the described tetrapeptide agents (45b, 46) were effective modifying agents when used with DPC-mediated siRNA delivery (U.S. Pat. Nos. 8,137,695 and 8,426,554), indicating rapid cleavage in the cell to release the membrane active polyamine. Effective in vitro knockdown also indicates that the presence of the PEG group did not adversely affect digestion of the linker in vivo. For dynamic polyconjugate delivery polymers modified with PEG$_{12}$ functionalized tetrapeptides, the order of increasing knockdown in vivo (45b>46>47) correlated with in vitro kinetic results. Validation of the in vitro model for kinetic evaluation was shown by the results obtained in animal studies.

TABLE 6

Normalized Factor VII levels after injection of polymer-siRNA conjugates targeted with acid-labile CDM-NAG[11].

| PEG-peptide modifying agent | Relative F VII activity |
|---|---|
| (45b) PEG-FCitAP-OSu | 40 ± 06 |
| (46) PEG-ACitAP-OSu | 66 ± 28 |
| (47) PEG-CitAP-OSu | 97 ± 34 |

Example 7

In Vivo Analysis of Lability.

The tetrapeptides were analyzed for in vivo lability and reversibility by testing the linkers as modifying agents for DPC-mediated siRNA delivery.

A) RNA Interference Triggers (siRNA).

siRNA synthesis: The control siRNAs of the following sequences were synthesized using standard phosphoramidite chemistry.

siF7 sense:

SEQ ID NO: 4
5'-(NH$_2$-C6)-GfcAfaAfgGfcGfuGfcCfaAfcUfcAf(invdT)-3' siF7 antisense:

SEQ ID NO: 6
5'dTsGfaGfuUfgGfcAfcGfcCfuUfuGfcdTsdT-3'

(lower case, 2'-OMe substitution; f, 2'-F substitution; d, 2'-deoxy substitution; and s, phosphorothioate linkage.)

Modifications of Amine siRNA with DBCO Disulfide:

DBCO-modified siRNAs were synthesized by reaction of 5' amine-modified siRNA with 1 weight equivalents (wt. eq.) of dibenzocyclooctyne-S—S—N-hydroxysuccinimidyl ester (ALDRICH catalogue #761532) and 0.36 wt. eq. of NaHCO$_3$ in water at 4° C. for 16 hours. The modified siRNAs were then precipitated by the addition of 9 volumes of ethanol and incubation at −80° C. for 2 h. The precipitate was dissolved in RNase-free PBS buffer and quantified by measuring absorbance at the 260 nm.

B) Polymer Synthesis:

RAFT copolymer of N-Boc-ethoxyethylamine acrylate and sec-butyl acrylate (EAB): Solutions of AIBN (1.00 mg/mL) and RAFT agent CPCPA (10.0 mg/mL) in butyl acetate were prepared. Monomer molar feed was 55% N-Boc-ethoxyethylamine acrylate, 45% sec-butyl acrylate (CAS #2998-08-5). Theoretical Mw was 100,000.

N-Boc-ethoxyethylamine acrylate (0.890 g, 3.43 mmol) sec-butyl acrylate (0.391 mL, 0.360 g, 2.81 mmol) CPCPA solution (0.350 mL, 0.0125 mmol), AIBN solution (0.308 mL, 0.00188 mmol), and butyl acetate (5.3 mL) were added to a 20 mL glass vial with stir bar. The vial was sealed with a septa cap and the solution bubbled with nitrogen using a long syringe with a second syringe as the outlet for 1 h. The syringes were removed and the vial heated to 80° C. for 16 h using an oil bath. The solution was allowed to cool to room temperature and transferred to a 50 mL centrifuge tube before hexane (35 mL) was added to the solution. The solution was centrifuged for 2 min at 4,400 rpm. The supernatant layer was carefully decanted and the bottom (solid or gel-like) layer was rinsed with hexane. The bottom layer was then re-dissolved in DCM (7 mL), precipitated in hexane (40 mL) and centrifuged once more. The supernatant was decanted and the bottom layer rinsed with hexane before the polymer was dried under reduced pressure for several hours. Yield of crude EAB copolymer was 0.856 g. Samples of the crude polymer were taken for multi-angle light scattering (MALS). The dried, crude copolymer was dissolved in DCM (100 mg/mL). Hexane was added until just after the cloud point was reached. The resulting milky solution was centrifuged. The bottom layer was extracted and fully precipitated into hexane. The fraction was centrifuged, after which the copolymer was isolated and dried under vacuum. Yield of isolated fraction of EAB copolymer was 0.478 g. Samples of the fractionated copolymer were taken for $^1$H-NMR and MALS. Composition determined by $^1$H-NMR was 61% N-Boc-ethoxyethylamine and acrylate, 39% sec-butyl acrylate.

MALS Analysis:

Approximately 10 mg of the copolymer was dissolved in 0.5 mL 75% dichloromethane, 20% tetrahydrofuran, 5% acetonitrile. The molecular weight and polydispersity (PDI) were measured using a Wyatt Heleos II multiangle light scattering detector attached to a Shimadzu Prominence HPLC using a Jordi 5µ 7.8×300 Mixed Bed LS DVB column. Crude Polymer: MW: 59,000 (PDI 1.3), Fractionated Polymer: MW 70,000 (PDI: 1.1).

Deprotection/Dialysis:

The dried samples were treated with 2M HCl in acetic acid (~7 ml) for 1 h to remove the BOC protecting groups. Then the reaction was diluted with 20 ml of water and allowed to stir for 10-15 min. The fractions were then dialyzed with 3500 MW dialysis tubing in high salt, high salt, and water for 15 h, 8 h, and 15 h respectively. The fractions were then transferred to 50 ml centrifuge tubes and lyophilized for 3 days or until dry. The dry samples were brought up at 20 mg/ml in water for further study.

C) Formation of Reversibly Modified siRNA Polyamine Conjugate:

Polyacrylate EAB in 5 mM pH 8.0 HEPES buffer was modified 1.5 wt % with a N-hydroxysuccinimidyl activated PEG$_4$ azide (Azido-dPEG$_4$-NHS ester from Quanta Biodesign) to provide azide groups for subsequent attachment of siRNA. The azide-modified polymer was then diluted to 5 mg/mL in 60 mg/mL HEPES base. To this solution was added 15 mg/mL (3 wt equivalents) of the indicated protease-cleavable PEG modifying reagents (the described herein tetrapeptide agents or PEG$_{12}$-FCit-PABC-PNP (8426554) to modify 40-50% of available amine groups. After 1 h, DBCO-modified rodent factor VII siRNA (0.25 wt eq relative to polymer) was added to polymer solution. After incubation overnight, conjugates were further modified by addition of molar excess relative to available amine groups of an N-acetylgalactosamine derivative CDM-NAG, NAG-A$^4$-A$^3$-A$^2$-A$^1$-NHS or NAG-ACit-PABC-PNP (U.S. Pat. No. 8,426,554, Rozema et al. 2015, Carlson et al. 2015), and incubated for 30 min to reversibly modify remaining polymer EAB amines.

D) In Vivo Assay.

Mice and Injection Procedures.

Male Wistar Han rats and female ICR mice, 6 to 8 weeks old, were obtained from Harlan Sprague-Dawley, (Indianapolis, Ind.). Animals were handled in accordance with animal used protocols approved by the Animal Care and Use Committee at Arrowhead Madison Inc. Rodents were maintained on a 12 hours light/dark cycle with free access to water and food (Harlan Teklad Rodent Diet, Harlan, Madison, Wis.). Animals were injected with 1 mg/kg polymer conjugated to 0.25 mg/kg siRNA. Samples were collected 5 days post injection.

Serum FVII Activity Measurements.

Serum samples were prepared by collecting blood by submandibular bleeding into microcentrifuge tubes containing 0.109 M sodium citrate anticoagulant (1 volume) following standard procedures. FVII activity in serum was measured with a chromogenic method using a test kit (BIOPHEN VII, Aniara, Mason, Ohio) following manufacturer's recommendations. Absorbance of colorimetric development was measured using a Tecan Safire-2 microplate reader at 405 nm.

The data in Table 7 show the tetrapeptide modified DPC delivery polymers were effective in delivery of siRNA in vivo. Further, the tetrapeptide agents were as effective as the previously described dipeptide-PABC modifying agents. Conjugates bearing 44a and 44b, containing the proteolytic FCitFP (SEQ ID NO: 12) tetramer, displayed equivalent activity to conjugates utilizing PABC mediated degradation for knockdown (Table 7). Effective siRNA delivery indicates effective modification and targeting of the polyamine and successful digestion and release of the polymer in hepatocytes after delivery to the cell.

In vivo activity and function correlated with in vitro digestion velocity data with FCitFP (SEQ ID NO: 12) modified DPC delivery polymers, showing better siRNA delivery than FCitAP modified DPC delivery polymers. Thus, the in vitro velocity of digestion data accurately predicted in vivo digestion and release data.

TABLE 7

Normalized Factor VII levels after injection of polymer-siRNA conjugates targeted with protease-labile NAG reagents.

| modifying agent | Relative Factor VII activity |
|---|---|
| Activity in mice | |
| (44a) PEG-FCitFP-OSu/(44b) NAG-FCitFP-OSu | 27 ± 06 |
| (45a) PEG-FCitAP-OSu/(45b) NAG-FCitAP-OSu | 48 ± 14 |
| PEG-FCit-PABC-PNP/NAG-ACit-PABC-PNP | 24 ± 11 |
| Activity in rats | |
| (44a) PEG-FCitFP-OSu/(44b) NAG-FCitFP-OSu | 26 ± 22 |
| (45a) PEG-FCitAP-OSu/(45b) NAG-FCitAP-OSu | 48 ± 8 |
| PEG-FCit-PABC-PNP/NAG-ACit-PABC-PNP | 30 ± 13 |

Example 8

RGD Mimic Tetrapeptides and PEG-Tetrapeptide Modified DPC Delivery Polymers.
A) Synthesis of APN 1170-100A (100A) and APN 1203-006 (006) Amphipathic Membrane Active Polyamines.

| Polymer | MW (protected) | Theoretical MW (deprotected) | PDI | % Amine Incorp. | % Alkyl Incorp. | % End Group Removal | Azides/ Polymer |
|---|---|---|---|---|---|---|---|
| APN 1170-100A | 64,430 | 45,765 | 1.22 | 56 | 44 | 0 | 1.25 |
| APN 1203-006 | 60,330 | 43,578 | 1.05 | 56 | 44 | 99 | 1.14 | i) Materials. 2,2'-Azobis(2,4-dimethyl valeronitrile) (V-65, radical initiator) was purchased from Wako Pure Chemical Industries. Propyl acrylate was purchased from Polysciences Inc. N-Boc-ethoxy-ethylamine acrylate was obtained from WuXi Inc. 2-(Dodecylthio-carbonothioylthio)-2-methylpropionic acid (DDMAT, RAFT Agent), 1,1'-Azobis-(cyclohexanecarbonitrile) (ACHN), 1-Ethylpiperidine hypophosphite (EHPH), Pentafluorophenol, N,N'-Dicyclohexylcarbodiimide and N,N-diisopropyl-ethylamine were purchased from Sigma Aldrich. O-(2-Aminoethyl)-O'-(2-azidoethyl)triethylene Glycol (azido-PEG$_4$-amine) was purchased from Biomatrik Inc.
ii). RAFT copolymer of N-Boc-ethoxyethylamine acrylate and propyl acrylate (EAP). Solutions of V-65 (2 mg/mL) and RAFT agent DDMAT (10 mg/mL) in butyl acetate were prepared. Monomer molar feed was 52% N-Boc-ethoxyethylamine acrylate, 48% propyl acrylate. Theoretical Mw was 75,000. RAFT agent (DDMAT) to initiator (V-65) molar ratio was 6.67:1.

N-Boc-ethoxyethylamine acrylate (1.778 g, 6.86 mmol), propyl acrylate (0.794 mL, 0.722 g, 6.33 mmol), DDMAT solution (1.215 mL, 0.0333 mmol), V-65 solution (0.621 mL, 0.005 mmol), and butyl acetate (10.2 mL) were added to a 20 mL glass vial with a stir bar. The vial was sealed with a septa cap and the solution bubbled with nitrogen using a long needle with a second needle as the outlet for 1 h. The needles were removed and the vial was heated to 50° C. for 24 h with stirring. The solution was allowed to cool to room temperature and transferred equally between two 50 mL centrifuge tube before hexane (35 mL) was added to both tubes. The solution was centrifuged for 2 min at 4400 rpm. The supernatant layer was carefully decanted and the bottom layer rinsed with hexane. The bottom layer of each tube was then re-dissolved in dichloromethane (7 mL), precipitated in hexane (40 mL) and centrifuged once more. The supernatant was decanted and the bottom layer rinsed with hexane before the layers were combined to one 50 mL centrifuge tube and the polymer was dried under reduced pressure for several hours. The yield of crude EAP copolymer was 2.1 g. Samples of the copolymer were taken for multi-angle light scattering (MALS), and $^1$H-NMR.

Polymer 006: The composition determined by $^1$H-NMR was 55% N-Boc-ethoxyethylamine acrylate and 45% propyl acrylate. The Mw for 006 determined by MALS was 58,600 g/mol with a polydispersity index (PDI) of 1.04.

Polymer 100A: Composition by 1H-NMR: 56% N-Boc-ethoxyethylamine acrylate and 44% propyl acrylate. MW by MALS: 65,150, PDI of 1.122.

iii). Radical induced co-end group removal (polymer 006 only). Solutions of 1,1'-Azobis-(cyclohexanecarbonitrile) (ACHN, 20 mg/mL) and 1-Ethylpiperidine hypophosphite (EPHP, 100 mg/mL) were prepared in toluene. EAP (2 g, 0.035 mmol), ACHN (0.213 mL, 0.5 eq, 0.0174 mmol), EPHP (1.25 mL, 20 eq, 0.697 mmol), and toluene (25.2 mL) were added to a 40 mL glass vial with a stir bar. The vial was sealed with a septa cap and the solution bubbled with nitrogen using a long needle with a second needle as the outlet for 1 h. The needles were removed and the vial was heated to 100° C. for 2 h. The solution was allowed to cool to room temperature and ~20 mL toluene was removed by rotary evaporation. The remaining solution was transferred to a 50 mL centrifuge vial, and hexane (35 mL) was added. The solution was centrifuged for 2 min at 4400 rpm. The supernatant layer was carefully decanted and the bottom layer rinsed with hexane. The bottom layer was then re-dissolved in dichloromethane (7 mL), precipitated in hexane (40 mL) and centrifuged once more. The supernatant was decanted and the bottom layer rinsed with hexane before the polymer was dried under reduced pressure for ~1 h. The polymer was dissolved in methyl tert-butyl ether (80 mL) and transferred to a separatory funnel. The solution was then washed with 3×30 mL volumes of H$_2$O followed by 3×30 mL volumes of saturated NaCl. The polymer solution was then dried over sodium sulfate, and vacuum filtered through 0.45 μm GHP filters. MTBE was removed via rotary evaporation and high vacuum. A sample was taken for monitoring of end group removal using a UV spectrophotometer. End group removal was calculated to be 99%. Samples were taken for MALS, GC-FID, and $^1$H-NMR. The composition of 006 by $^1$H-NMR was 55% N-Boc-ethoxyethylamine acrylate and 45% propyl acrylate. The conversion of 006 determined by GC-FID was 81.4% for the N-Boc-ethoxyethylamine acrylate and 77.3% for the propyl acrylate. The conversion of 100A determined by GC-FID conversion was 87% for N-Boc-ethoxyethylamine acrylate and 83% for propyl acrylate. The Mw for polymer 006 determined by MALS was 57,700 g/mol with a polydispersity index (PDI) of 1.06.

iv). Pentafluorophenol activation of α-end group. EAP polymer (2 g, 0.0347 mmol), pentafluorophenol (63.8 mg, 0.3466 mmol), N,N'-Dicyclohexylcarbodiimide (71.5 mg, 0.3466 mmol), and dichloromethane (40 mL) were added to a 100 mL round bottom flask with a stir bar. The flask was stoppered with a rubber septum and the system was purged with nitrogen for 15 min. The solution was stirred for 16 h at room temperature. Additional Pentafluorophenol (63.8 mg, 0.3466 mmol) and N,N'-Dicyclohexylcarbodiimide (71.5 mg, 0.3466 mmol) were added, the flask stoppered with a rubber septum, and the system was purged with nitrogen for 15 min. The solution was stirred for 3 h at room temperature. The polymer was precipitated with hexane (~10x volume), centrifuged, and the solvent was decanted. The polymer was dissolved in minimal dichloromethane, precipitated with hexane (~10x volume), centrifuged, and the solvent was decanted. The polymer was dissolved in minimal ethyl acetate, precipitated with hexane (~10x volume), centrifuged, and the solvent was decanted. The polymer precipitate was dried under high vacuum until the solid reached a constant weight.

v). Azide functionalization of α-end group. In a 100 ml round bottom flask equipped with a rubber septum and stir bar, polymer from the previous step (1.9 g, 0.0329 mmol) was dissolved in dichloromethane (38 mL). Azido-PEG$_4$-Amine (86.4 mg, 0.3293 mmol) and N,N-Diisopropylethylamine (46.8 mg, 63.1 µL, 0.3622 mmol) were added to the flask with stirring. The system was purged with nitrogen for 15 min, and the reaction was left to stir at room temperature overnight. Additional Azido PEG$_4$ Amine (86.4 mg, 0.3293 mmol) and N,N-Diisopropylethylamine (46.8 mg, 63.1 µL, 0.3622 mmol) were added to the flask, the system was purged with N$_2$ gas, and the reaction was stirred for 3 h at room temperature. The polymer was precipitated with hexane (~10x volume), centrifuged, and the solvent was decanted. The polymer was dissolved in minimal dichloromethane, precipitated with hexane (~10x volume), centrifuged, and the solvent was decanted. The polymer precipitate was dried under high vacuum until the solid reached a constant weight. The yield of Azide functionalized EAP was 1.77 g. Samples of the copolymer were taken for multi-angle light scattering (MALS), and $^1$H-NMR.

Polymer 006: The composition determined by $^1$H-NMR was 56% N-Boc-ethoxyethylamine acrylate and 44% propyl acrylate. The Mw determined by MALS was 60,330 g/mol with a polydispersity index (PDI) of 1.05.

Polymer 100A: The composition by $^1$H-NMR was 56% N-Boc-ethoxyethylamine acrylate and 44% propyl acrylate. The Mw determined by MALS: 64,430 with PDI of 1.217.

Mono-Azide: The term "mono-azide" or "mono-azide polymer" indicates that steps D and E of the procedures above were done and an azide group was coupled to the α-end group of the polymer.

vi). Boc Deprotection and Tangential Flow Filtration. In a 100 mL round bottom flask, 2M HCl in acetic acid (28 mL) was added to Azide functionalized EAP copolymer (1.67 g, 0.0277 mmol). The reaction was stirred at room temperature for 1 h. De-ionized H$_2$O (56 mL) was added, and stirred for 10 min. The solution was then immediately exchanged with 10 equivalent volumes of 5 mM Phosphate-Citrate buffer (pH 5) using a mPES 30 kD 115 cm$^2$ filter module equipped with a tangential flow filtration system (KrosFlo Research). The solution was then concentrated using the apparatus to 55 mL final volume. A pH value of 5.1 was recorded. Samples were taken for concentration determination by headspace gas chromatography. An aliquot was lyophilized and then reconstituted in 33.3% Acetonitrile-d in Deuterium Oxide at a concentration of 10 mg/mL for $^1$H-NMR analysis. Theoretical MW was calculated to be 43,026 g/mol 45,765 g/mol for 006 and 100A respectively.

vii). Using similar techniques, similar amphipathic membrane active polyamines can be readily formed. Particularly, amphipathic membrane active polyamines with molecular weight (Mw) 40-120 k protected (25 k to 85 k deprotected), PDI ranges of 1.03 to 1.2, and monomer ratios of 35% amine monomer/65% hydrophobic group monomer to 70% amine monomer/30% hydrophobic group monomer.

B) Synthesis of APN 1095-126 (126).

| MW (protected) | Theoretical MW (deprotected) | PDI | % Amine Incorporation | % Alkyl Incorporation | % End Group Removal | Azides Per Polymer |
|---|---|---|---|---|---|---|
| 66,670 | 47,606 | 1.11 | 56 | 44 | 0 | 4.1 |

Synthesis of APN 1095-126 used dithiobenzoate moiety RAFT agent and AIBN RAFT initiator, compared to the trithiocarbonate moiety RAFT agent and V-65 RAFT initiator used for synthesis of 100A and 006. The conditions for this polymerization required different heating temperatures and times. In addition, this polymer required fractional precipitation. The polymer was not endcapped, but the method of azide addition was the same as 100A and 006.

i). Materials. Propyl acrylate was purchased from Polysciences Inc. N-Boc-ethoxyethylamine acrylate was obtained from WuXi Inc. 4-Cyano-4-(phenylcarbonothioylthio) pentanoic acid (CPCPA, RAFT Agent), 2,2'-Azobis(2-methylpropionitrile) (AIBN, radical initiator), Pentafluorophenol, N,N'-Dicyclohexylcarbodiimide and N,N-diisopropylethylamine were purchased from Sigma Aldrich. O-(2-Aminoethyl)-O'-(2-azidoethyl)triethylene Glycol (azido-PEG$_4$-amine) was purchased from Biomatrik Inc.

ii) RAFT copolymer of N-Boc-ethoxyethylamine acrylate and propyl acrylate (EAP). The following procedure was repeated 8 times to yield a total of 4.5513 g fractionated EAP copolymer. Solutions of AIBN (1.035 mg/mL) and RAFT agent CPCPA (50.54 mg/mL) in butyl acetate were prepared.

Monomer molar feed was 52% N-Boc-ethoxyethylamine acrylate, 48% propyl acrylate. Theoretical Mw was 75,000. RAFT agent (CPCPA) to initiator (AIBN) molar ratio was 6.67:1.

N-Boc-ethoxyethylamine acrylate (1.7879 g, 6.9 mmol), propyl acrylate (0.774 mL, 0.7121 g, 6.24 mmol), CPCPA solution (0.184 mL, 0.0333 mmol), AIBN solution (0.793 mL, 0.005 mmol), and butyl acetate (11.02 mL) were added to a 20 mL glass vial with a stir bar. The vial was sealed with a septa cap and the solution bubbled with nitrogen using a long needle with a second needle as the outlet for 1 h. The needles were removed and the vial was heated to 50° C. for 24 h with stirring. The solution was allowed to cool to room temperature and transferred to a 50 mL centrifuge tube before hexane (35 mL) was added. The solution was centrifuged for 2 min at 4400 rpm. The supernatant layer was carefully decanted and the bottom layer rinsed with hexane. The bottom layer of each tube was then re-dissolved in dichloromethane (7 mL), precipitated in hexane (40 mL) and centrifuged once more. The supernatant was decanted and the bottom layer rinsed with Hexane before the polymer was dried under reduced pressure for several hours. The yield of crude EAP copolymer was 1.734 g. Samples of the crude copolymer were taken for multi-angle light scattering (MALS), and $^1$H-NMR. The dried, crude copolymer was dissolved in DCM (100 mg/mL). Hexane was added until just after the cloud point was reached. The resulting milky solution was centrifuged. The bottom layer was extracted and fully precipitated into hexane. The fraction was centrifuged, after which the copolymer was isolated and dried under vacuum. The yield of isolated fraction of EAP copolymer was 0.602 g. Samples of the fractionated copolymer were taken for $^1$H-NMR and MALS. The composition determined by $^1$H-NMR was 56% N-Boc-ethoxyethylamine acrylate and 44% propyl acrylate. The Mw determined by MALS was 62,010 g/mol with a polydispersity index (PDI) of 1.14.

iii). Pentafluorophenol activation of α-end group. EAP polymer (2 g, 0.0347 mmol), pentafluorophenol (63.8 mg, 0.3466 mmol), N,N'-Dicyclohexylcarbodiimide (71.5 mg, 0.3466 mmol), and dichloromethane (40 mL) were added to a 100 mL round bottom flask with a stir bar. The flask was stoppered with a rubber septum and the system was purged with nitrogen for 15 min. The solution was stirred for 16 h at room temperature. Additional Pentafluorophenol (63.8 mg, 0.3466 mmol) and N,N'-Dicyclohexylcarbodiimide (71.5 mg, 0.3466 mmol) were added, the flask stoppered with a rubber septum, and the system was purged with nitrogen for 15 min. The solution was stirred for 3 h at room temperature. The polymer was precipitated with hexane (~10× volume), centrifuged, and the solvent was decanted. The polymer was dissolved in minimal dichloromethane, precipitated with hexane (~10× volume), centrifuged, and the solvent was decanted. The polymer was dissolved in minimal ethyl acetate, precipitated with hexane (~10× volume), centrifuged, and the solvent was decanted. The polymer precipitate was dried under high vacuum until the solid reached a constant weight.

iv). Azide functionalization of α-end group. In a 100 ml round bottom flask equipped with a rubber septum and stir bar, polymer from the previous step (1.9 g, 0.0329 mmol) was dissolved in dichloromethane (38 mL). Azido-PEG$_4$-Amine (86.4 mg, 0.3293 mmol) and N,N-Diisopropyl-ethylamine (46.8 mg, 63.1 μL, 0.3622 mmol) were added to the flask with stirring. The system was purged with nitrogen for 15 min, and the reaction was left to stir at room temperature overnight. Additional Azido PEG$_4$ Amine (86.4 mg, 0.3293 mmol) and N,N-Diisopropyl-ethylamine (46.8 mg, 63.1 μL, 0.3622 mmol) were added to the flask, the system was purged with N$_2$ gas, and the reaction was stirred for 3 h at room temperature. The polymer was precipitated with hexane (~10× volume), centrifuged, and the solvent was decanted. The polymer was dissolved in minimal dichloromethane, precipitated with hexane (~10× volume), centrifuged, and the solvent was decanted. The polymer precipitate was dried under high vacuum until the solid reached a constant weight. The yield of Azide functionalized EAP was 1.77 g. Samples of the copolymer were taken for multi-angle light scattering (MALS), and $^1$H-NMR. The composition determined by $^1$H-NMR was 56% N-Boc-ethoxyethylamine acrylate and 44% propyl acrylate. The Mw determined by MALS was 66,670 g/mol with a polydispersity index (PDI) of 1.11.

v). Boc Deprotection and Tangential Flow Filtration. In a 100 mL round bottom flask, 2M HCl in acetic acid (28 mL) was added to Azide functionalized EAP copolymer (1.67 g, 0.0277 mmol). The reaction was stirred at room temperature for 1 hour. De-ionized H$_2$O (56 mL) was added, and stirred for 10 min. The solution was then immediately exchanged with 10 equivalent volumes of 5 mM Phosphate-Citrate buffer (pH 5) using a mPES 30 kD 115 cm$^2$ filter module equipped with a tangential flow filtration system (KrosFlo Research). The solution was then concentrated using the apparatus to 55 mL final volume. A pH value of 5.1 was recorded. Samples were taken for concentration determination by headspace gas chromatography. An aliquot was lyophilized and then reconstituted in 33.3% Acetonitrile-d in Deuterium Oxide at a concentration of 10 mg/mL for $^1$H-NMR analysis. Theoretical MW was calculated to be 43,026 g/mol.

C). RGD-PEG$_n$-FCitFP-TFP and PEG$_n$-FCitFP-TFP Agent Synthesis.

The modifying agent precursor (di-Boc)RGD(OtBu)-APBA-PEG$_n$-FCitFP-COOH was prepared using general Fmoc chemistry solid phase synthesis using 2-Cl-Trt resin preloaded with Fmoc-Proline-OH. To Resin-Pro-Fmoc was added sequentially (following Fmoc deprotection at each step): FMoc-Phe-OH, Fmoc-Cit-OH, Fmoc-Phe-OH, Fmoc-NH-PEG$_n$-COOH, 4-(N-Fmoc-p-aminophenoxy)-butyric acid (APBA), Fmoc-Asp(OtBu)-OH, Fmoc-Gly-OH, and diboc-m-guanidino benzoic acid.

(diboc)RGD(OtBu)-APBA-PEG$_n$-FCitFP-COOH (458 mg, 0.200 mmols) and TFP (66.5 mg, 0.400 mmols) were dissolved in anhydrous DCM (5.0 mL) and cooled to 0° C. in an ice/water bath while stirring under Argon. EDC (77 mg, 0.400 mmols) was added and the reaction mixture stirred in an ice/water bath at 0° C. for 30 min. Reaction progress was monitored by TLC (8.5:1.5 CHCl$_3$:MeOH) and was complete after 90 min with no starting material observed by TLC. The reaction mixture was diluted to 100 mL total volume with DCM, washed 3×40 mL with DI H$_2$O (pH=5), and washed 1×40 mL aqueous saturated NaCl solution. The organics were then dried over Na$_2$SO$_4$, and concentrated on a rotovap to yield 448 mg (92% yield) of a tan/orange foam. The structure was confirmed by $^1$H NMR, and ESI MS (Reaction shown above for PEG$_{20}$ (n=20)).

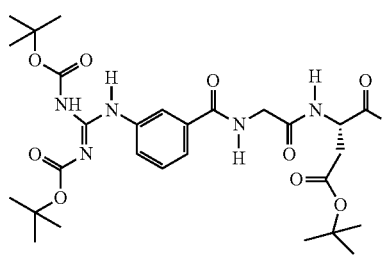
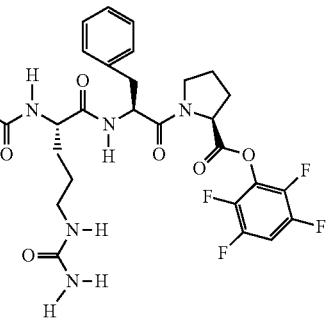

(diboc)RGD(OtBu)-APBA-PEG$_n$-FCitFP-TFP
(shown for n = 20)

(diboc)RGD(OtBu)-PEGn-FCitFP-TFP (497 mg, 0.204 mmols) was dissolved in [9.25:0.75:0.50]TFA:H$_2$O:Thioanisole (5.0 mL) and stirred at room temperature in a closed flask for 45 min. Reaction completion was confirmed by MS (ESI, scan neg, 300-3000) with no masses related to starting material or partially deprotected intermediates observed. The reaction mixture was then precipitated into 45 mL diethyl ether, spun down, the supernatant poured off, and washed 2×10 mL diethyl ether and dried on high vacuum overnight. The final product was purified on prep HPLC using a Thermo Aquasil C18 5 um semi prep column, with mobile phases 0.1% TFA in H$_2$O and ACN. Each injection was 50 mg of crude material dissolved in 3.0 mL of 0.1% TFA in [61:39]H$_2$O:ACN run on a gradient of (indicated in % B) 39-(5)-39-(35)-43-(5)-95-(10)-95-(2)-39-(5)-39. Each sample for injection was prepared (dissolved) within 15 minutes of being injected and positive fractions were pooled in one flask and kept cold in the freezer until the last injection of the day had finished. The positive fractions were then concentrated on the rotovap with a bath temperature of 32° C. to dryness, then chased 2× with ACN/Toluene, then 3× with ACN and then dried on high vacuum overnight. Out of 257 mg injected crude, 180 mg (70%) was isolated as pure material (Reaction shown above for PEG$_{20}$ (n=20)).

4-(N-Fmoc-p-aminophenoxy)-butyric acid 1 synthesis. p-Nitro-phenol (2) (7.5 g, 53.9 mmole) was combined with ethyl 4-bromobutyrate (8.45 ml, 59 mmol) and K$_2$CO$_3$ (7.5 g, 54 mmole) in DMF (75 mL). The mixture was stirred for 2 h at 100° C. DMF was removed and the crude product was diluted in a mixture of 3:1 mixture of 2 N NaOH and methanol and stirred 4 h at RT. The reaction mixture was acidified with 6 M HCl. The white precipitate was collected to yield 4-(p-Nitrophenyloxy)-butyric acid 3: (10.9 g, 90% yield).

4-(p-Nitrophenyloxy)-butyric acid 3 (37.1 g, 165 mmole) was dissolved in MeOH (1 L) with ammonium formate (35 g, 555 mmole) and 10% Pd/C (Degussa Type) (3.5 g) was added. The mixture was refluxed at 65° C. overnight. The reaction was filtered with celite to yield a reddish brown solid of product 4-(p-Aminophenyloxy)-butyric acid 4 (30.5 g, 95% yield).

4-(p-Aminophenyloxy)-butyric acid 4 (5.1 g, 26 mmole) was dissolved in 6:4 a mixture of an aqueous saturated NaHCO$_3$ (3.36 g, 40 mmol) in H$_2$O (450 mL) and THF (300 ml) to make a white slurry. Fmoc-OSu (8.82 g, 26.1 mmole) was added and the reaction was stirred for 4 h. The acetone was removed, the reaction was acidified (HCl), and the off-white precipitate was collected and triturated in 1N HCl to yield 9.6 g of product 4-(N-Fmoc-p-aminophenoxy)-butyric acid 1 (88% yield).

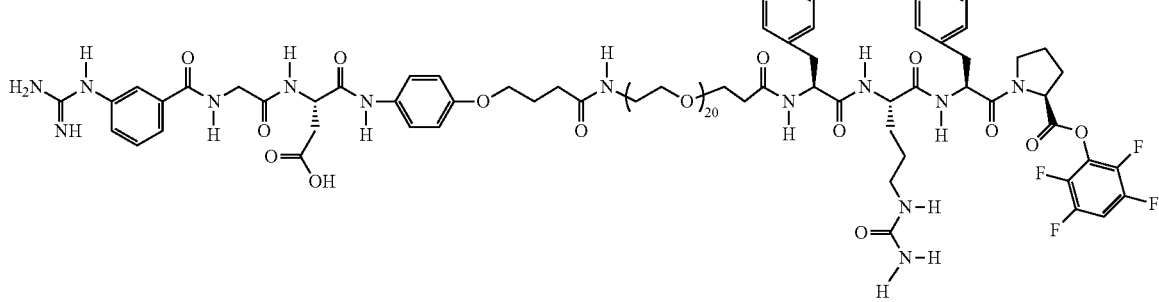

RGD-PEG$_n$-FCitFP-TFP
(shown for n = 20)

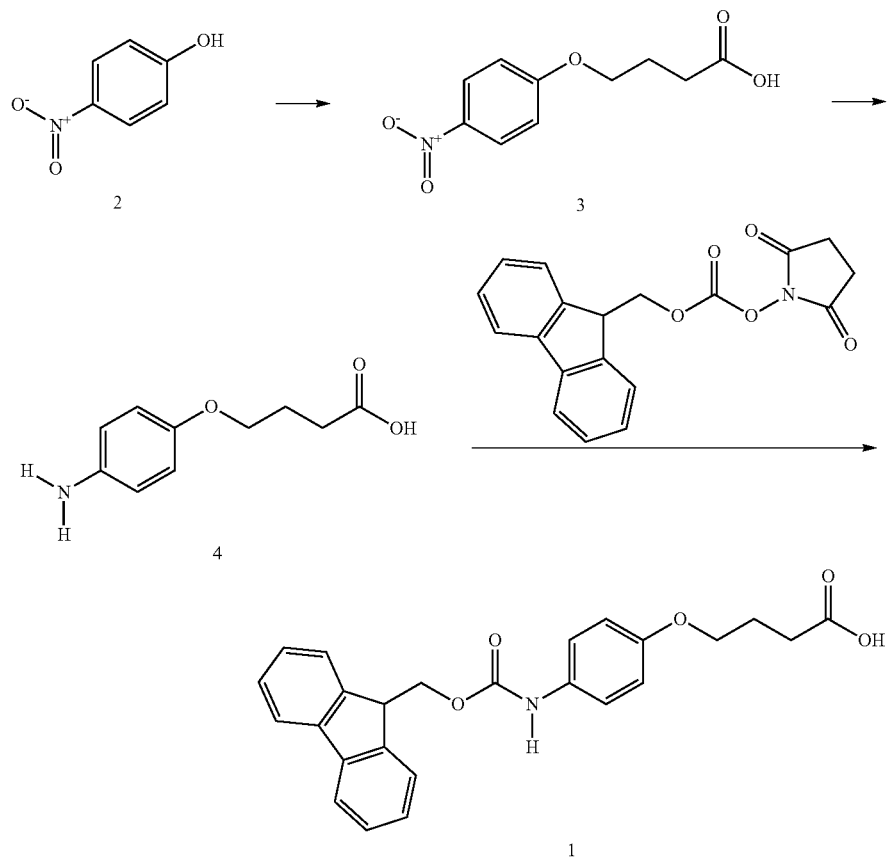

diBoc-m-guanidino-benzoic acid 5 was synthesized according to Riches A G et al. Tetrahedron (2012) 68, p. 9448-9455.

PEG$_n$-FCitFP modifying agents were made using similar chemistry.

D) Masking (Modification) of Polymer

The mono azide-polymer was reacted with protease cleavable-RGD agent (RGD-PEG$_8$-ACit-PNP, RDG-PEG$_8$-FCitFP-TFP, RGD-PEG$_{15}$-FCitFP-TFP, RGD-PEG$_{19}$-FCitFP-TFP, or RGD-PEG$_{20}$-FCitFP-TFP) at weight ratios of 1:0.125, 1:0.25, 1:0.5, 1:1, 1:1.5, 1:2 (polymer:RGD) in 50 mM HEPES, pH 8.5 buffer for 4 h at RT. The modified polymer was then reacted with protease cleavable-PEG agent (PEG$_6$-ACit-PABC-PNP, PEG$_{12}$-ACit-PABC-PNP, PEG$_{12}$-FCit-PABC-PNP, PEG$_{12}$-FCitFP-TFP) at a weight ratio of 1:8 (polymer:PEG) in 50 mM HEPES, pH 8.5 buffer for 2 h at RT. Alkyne-RNAi trigger at a weight ratio of 1:0.3 (polymer:Alkyne-RNAi trigger) was added to the modified polymer in 100 mM sodium acetate-acetic acid buffer solution, pH 5.0 for 5 days at RT. The completed conjugate was TFF purified and conjugation efficiency determined.

E) Evaluation of In Vivo Delivery Using Tetrapeptide Modified DPC Delivery Polymers.

Kidney RCC tumor-bearing mice were treated with a single tail vein injection of isotonic glucose (G1) or the indicated Hif2α-ITG-DPC (Hif2α-ITG-DPC=Hif2a RNAi trigger-delivery polymer conjugate. The delivery polymer is modified with RGD ligand and PEG modifying agents). Mice were euthanized 72 h after injection and total RNA was prepared from kidney tumor using Trizol reagent following manufacture's recommendation. Relative HiF2α mRNA levels were determined by RT-qPCR as described below and compared to mice treated with delivery buffer (isotonic glucose) only (Table 8).

TABLE 8

| HiF2α RNAi trigger | | RGD agent | | | | Rel Exp day 4 | | |
| ID | μg | μg | polymer identity | modif. level | RGD/polymer | PEG agent | ave. | low error | high error |
| --- | --- | --- | --- | --- | --- | --- | --- | --- | --- |
| — | | | | | | | 1.000 | 0.060 | 0.064 |
| AD01031 | 80 | 280 | RGD-PEG8-HyNic | | | PEG12-AC-PABC | 0.300 | 0.074 | 0.098 |
| AD01031 | 80 | 280 | RGD-PEG8-AC-PABC | 0.4× | | PEG6-AC-PABC | 0.311 | 0.055 | 0.067 |
| AD01214 | 80 | 280 | RGD-PEG8-HyNic | | | PEG12-FC-PABC | 0.489 | 0.022 | 0.023 |
| AD01214 | 80 | 280 | RGD-PEG8-HyNic | | | PEG12-FCFP-TFP | 0.210 | 0.032 | 0.038 |
| AD01214 | 80 | 280 | RGD-PEG-AC-PABC | | | PEG6-AC-PABC | 0.360 | 0.019 | 0.021 |
| AD01214 | 80 | 280 | RGD-PEG8-ACFP | 1× | | PEG6-AC-PABC | 0.288 | 0.005 | 0.005 |

TABLE 8-continued

| HiF2α RNAi trigger | | RGD agent | | | | Rel Exp day 4 | | |
|---|---|---|---|---|---|---|---|---|
| ID | μg | polymer identity | modif. level | RGD/polymer | PEG agent | ave. | low error | high error |
| AD01214 | 115 | 375 | RGD-PEG8-HyNic | | | PEG12-FCFP-TFP | 0.258 | 0.033 | 0.038 |
| AD01214 | 112.5 | 375 | RGD-PEG15-FCFP-TFP | 0.5× | 10.8 | PEG12-AC-PABC | 0.193 | 0.046 | 0.061 |
| AD01214 | 112.5 | 375 | RGD-PEG15-FCFP-TFP | 1× | 16.1 | PEG12-AC-PABC | 0.182 | 0.007 | 0.008 |
| AD01214 | 112.5 | 375 | RGD-PEG15-FCFP-TFP | 2× | 29.0 | PEG12-AC-PABC | 0.182 | 0.031 | 0.038 |
| AD01214 | 112.5 | 375 | RGD-PEG19-FCFP-TFP | 0.5× | 10.7 | PEG12-AC-PABC | 0.163 | 0.023 | 0.027 |
| AD01214 | 112.5 | 375 | RGD-PEG19-FCFP-TFP | 1× | 18.5 | PEG12-AC-PABC | 0.114 | 0.011 | 0.012 |
| AD01214 | 112.5 | 375 | RGD-PEG19-FCFP-TFP | 2× | 31.1 | PEG12-AC-PABC | 0.182 | 0.047 | 0.063 |
| AD01214 | 112.5 | 375 | RGD-PEG15-FCFP-TFP | 1× | | PEG12-FCFP-TFP | 0.148 | 0.079 | 0.169 |
| AD01214 | 112.5 | 375 | RGD-PEG19-FCFP-TFP | 1× | | PEG12-FCFP-TFP | 0.188 | 0.026 | 0.030 |
| AD01214 | 112.5 | 300 | RGD-PEG8-HyNic | | | PEG12-AC-PABC | 0.357 | 0.069 | 0.086 |
| AD01214 | 112.5 | 375 | RGD-PEG20-FCFP-TFP | 0.125× | 1.9 | PEG12-AC-PABC | 0.169 | 0.052 | 0.075 |
| AD01214 | 112.5 | 375 | RGD-PEG20-FCFP-TFP | 0.25× | 3.4 | PEG12-AC-PABC | 0.168 | 0.029 | 0.035 |
| AD01214 | 112.5 | 375 | RGD-PEG20-FCFP-TFP | 0.5× | 6.6 | PEG12-AC-PABC | 0.130 | 0.004 | 0.005 |
| AD01214 | 112.5 | 375 | RGD-PEG20-FCFP-TFP | 1× | 13 | PEG12-AC-PABC | 0.121 | 0.016 | 0.018 |
| AD01214 | 112.5 | 375 | RGD-PEG20-FCFP-TFP | 1.5× | 20 | PEG12-AC-PABC | 0.135 | 0.018 | 0.020 |

Example 9

Additional Structures Illustrating Utility of the Described Tetrapeptide Linkers.

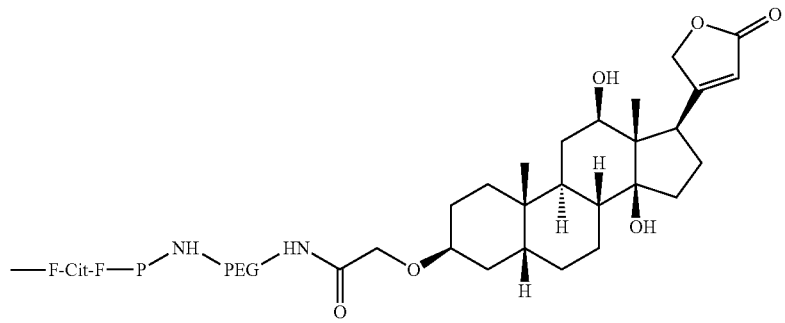

$R^5$-FCitFP-Digoxin (drug molecule)

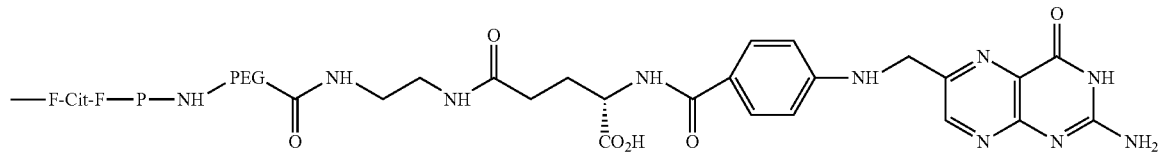

$R^5$-FCitFP-Folate (cell receptor ligand)

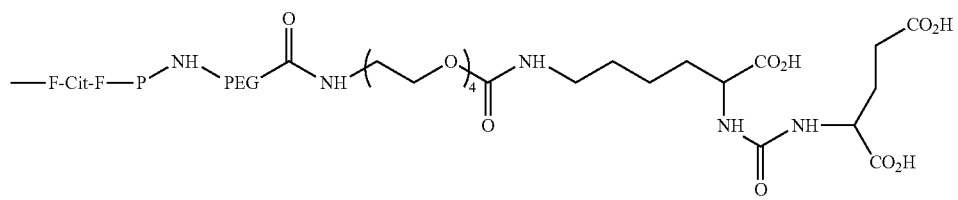

$R^5$-FCitFP-PSMA

-continued

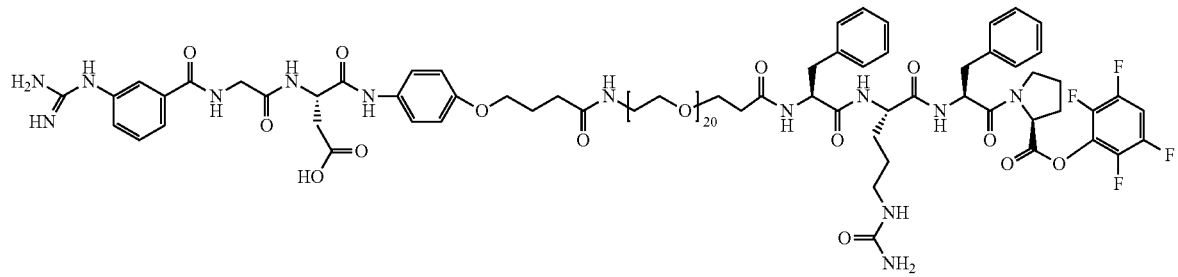

RGD-FCitFP-TFT reactive group (cell receptor (RGD mimic-containing modifying agent)

The invention claimed is:

1. A tetrapeptide linker comprising the structure represented by:

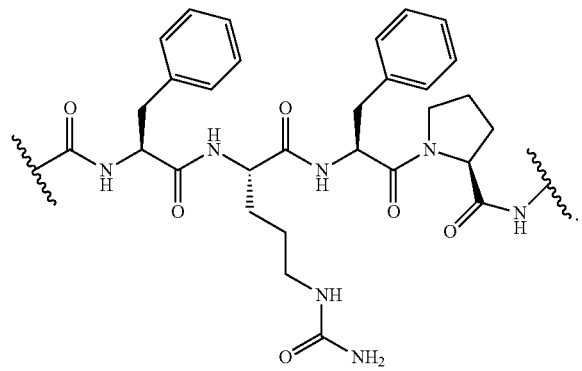 [SMILES: *NC(=O)[C@@H]1CCCN1C(=O)[C@H](Cc1ccccc1)NC(=O)[C@H](CCCNC(N)=O)NC(=O)[C@H](Cc1ccccc1)NC(*)=O]

2. The tetrapeptide linker of claim 1, wherein the tetrapeptide linker is linked to: (a) a first compound that comprises a targeting group, a steric stabilizer, a polynucleotide, a polymer, a polyamine, an antibody, a drug product, a hapten, a digoxigenin, a vitamin, a biotin, a fluorophore, an antibody, a monoclonal antibody, or an antibody fragment; and (b) a second compound that comprises a targeting group, a steric stabilizer, a polynucleotide, a polymer, a polyamine, an antibody, a drug product, a hapten, a digoxigenin, a vitamin, a biotin, a fluorophore, an antibody, a monoclonal antibody, or an antibody fragment.

3. The tetrapeptide linker of claim 2, wherein the tetrapeptide linker is linked to the first compound and/or to the second compound via an amide bond.

4. The tetrapeptide linker of claim 2, wherein the second compound comprises a polyamine.

5. The tetrapeptide linker of claim 2, wherein the first compound and/or the second compound comprises a targeting group.

6. The tetrapeptide linker of claim 5, wherein the targeting group comprises a cell receptor ligand.

7. The tetrapeptide linker of claim 2, wherein the first compound and/or the second compound comprises a drug product.

8. The tetrapeptide linker of claim 2, wherein the first compound and/or the second compound comprises a steric stabilizer.

9. The tetrapeptide linker of claim 8, wherein the steric stabilizer is polyethylene glycol (PEG).

10. The tetrapeptide linker of claim 2, wherein the first compound and/or the second compound comprises a cell receptor ligand having affinity for an integrin.

11. The tetrapeptide linker of claim 10, wherein the integrin is an αvβ3 integrin.

12. The tetrapeptide linker of claim 10, wherein the integrin is an αvβ6 integrin.

13. The tetrapeptide linker of claim 10, wherein the cell receptor ligand having affinity for an integrin comprises an RGD-containing peptide.

14. The tetrapeptide linker of claim 2, wherein the first compound and/or the second compound comprises an asialoglycoprotein receptor (ASGPr) ligand.

15. The tetrapeptide linker of claim 13, wherein the asialoglycoprotein receptor (ASGPr) ligand comprises N-acetylgalactosamine.

16. The tetrapeptide linker of claim 2, wherein the first compound and/or the second compound comprises a polynucleotide.

17. The tetrapeptide linker of claim of claim 15, wherein the polynucleotide is an RNAi trigger.

18. The tetrapeptide linker of claim 1, wherein the tetrapeptide linker is linked to an RNAi trigger and to a targeting group.

19. The tetrapeptide linker of claim 18, wherein the targeting group comprises a cell receptor ligand.

20. The tetrapeptide linker of claim 19, wherein the cell receptor ligand comprises an asialoglycoprotein receptor (ASGPr) ligand and/or a ligand having affinity for an integrin.

21. A method of inhibiting expression of a gene, the method comprising administering to a subject a composition comprising the tetrapeptide linker of claim 18.

* * * * *

SEQUENCE LISTING

```
<160> NUMBER OF SEQ ID NOS: 19

<210> SEQ ID NO 1
<211> LENGTH: 4
<212> TYPE: PRT
<213> ORGANISM: Artificial Sequence
<220> FEATURE:
<223> OTHER INFORMATION: tetrapeptide
<220> FEATURE:
<221> NAME/KEY: MISC_FEATURE
<222> LOCATION: (2)..(2)
<223> OTHER INFORMATION: Xaa = Citrulline

<400> SEQUENCE: 1

Ala Xaa Ala Ala
1

<210> SEQ ID NO 2
<211> LENGTH: 4
<212> TYPE: PRT
<213> ORGANISM: Artificial Sequence
<220> FEATURE:
<223> OTHER INFORMATION: tetrapeptide
<220> FEATURE:
<221> NAME/KEY: MISC_FEATURE
<222> LOCATION: (2)..(2)
<223> OTHER INFORMATION: Xaa = citrulline

<400> SEQUENCE: 2

Ala Xaa Ala Pro
1

<210> SEQ ID NO 3
<211> LENGTH: 4
<212> TYPE: PRT
<213> ORGANISM: Artificial Sequence
<220> FEATURE:
<223> OTHER INFORMATION: tetrapeptide
<220> FEATURE:
<221> NAME/KEY: MISC_FEATURE
<222> LOCATION: (2)..(2)
<223> OTHER INFORMATION: Xaa = citrulline

<400> SEQUENCE: 3

Ala Xaa Phe Pro
1

<210> SEQ ID NO 4
<211> LENGTH: 20
<212> TYPE: DNA
<213> ORGANISM: Artificial Sequence
<220> FEATURE:
```

```
<223> OTHER INFORMATION: Factor 7 siRNA sense strand
<220> FEATURE:
<221> NAME/KEY: modified_base
<222> LOCATION: (1)..(19)
<223> OTHER INFORMATION: ribonucleotide

<400> SEQUENCE: 4
gcaaaggcgu gccaacucat                                              20

<210> SEQ ID NO 5
<211> LENGTH: 4
<212> TYPE: PRT
<213> ORGANISM: Artificial Sequence
<220> FEATURE:
<223> OTHER INFORMATION: tetrapeptide
<220> FEATURE:
<221> NAME/KEY: MISC_FEATURE
<222> LOCATION: (1)..(1)
<223> OTHER INFORMATION: Xaa = Citrulline

<400> SEQUENCE: 5

Xaa Ala Ala Ala
1

<210> SEQ ID NO 6
<211> LENGTH: 21
<212> TYPE: DNA
<213> ORGANISM: Artificial Sequence
<220> FEATURE:
<223> OTHER INFORMATION: Factor 7 siRNA antisense strand
<220> FEATURE:
<221> NAME/KEY: modified_base
<222> LOCATION: (2)..(19)
<223> OTHER INFORMATION: ribonucleotide

<400> SEQUENCE: 6
tgaguuggca cgccuuugct t                                            21

<210> SEQ ID NO 7
<211> LENGTH: 4
<212> TYPE: PRT
<213> ORGANISM: Artificial Sequence
<220> FEATURE:
<223> OTHER INFORMATION: tetrapeptide
<220> FEATURE:
<221> NAME/KEY: MISC_FEATURE
<222> LOCATION: (2)..(2)
<223> OTHER INFORMATION: Xaa = Citrulline

<400> SEQUENCE: 7

Phe Xaa Ala Ala
1

<210> SEQ ID NO 8
<211> LENGTH: 4
<212> TYPE: PRT
<213> ORGANISM: Artificial Sequence
<220> FEATURE:
<223> OTHER INFORMATION: tetrapeptide
<220> FEATURE:
<221> NAME/KEY: MISC_FEATURE
<222> LOCATION: (2)..(2)
<223> OTHER INFORMATION: Xaa = Citrulline

<400> SEQUENCE: 8

Phe Xaa Ala Pro
1

<210> SEQ ID NO 9
```

```
<211> LENGTH: 4
<212> TYPE: PRT
<213> ORGANISM: Artificial Sequence
<220> FEATURE:
<223> OTHER INFORMATION: tetrapeptide
<220> FEATURE:
<221> NAME/KEY: MISC_FEATURE
<222> LOCATION: (2)..(2)
<223> OTHER INFORMATION: Xaa = Citrulline
<220> FEATURE:
<221> NAME/KEY: MISC_FEATURE
<222> LOCATION: (4)..(4)
<223> OTHER INFORMATION: Xaa = N-methyl alanine

<400> SEQUENCE: 9

Phe Xaa Phe Xaa
1

<210> SEQ ID NO 10
<211> LENGTH: 4
<212> TYPE: PRT
<213> ORGANISM: Artificial Sequence
<220> FEATURE:
<223> OTHER INFORMATION: tetrapeptide
<220> FEATURE:
<221> NAME/KEY: MISC_FEATURE
<222> LOCATION: (2)..(2)
<223> OTHER INFORMATION: Xaa = Citrulline

<400> SEQUENCE: 10

Phe Xaa Phe Ala
1

<210> SEQ ID NO 11
<211> LENGTH: 4
<212> TYPE: PRT
<213> ORGANISM: Artificial Sequence
<220> FEATURE:
<223> OTHER INFORMATION: tetrapeptide
<220> FEATURE:
<221> NAME/KEY: MISC_FEATURE
<222> LOCATION: (2)..(2)
<223> OTHER INFORMATION: Xaa = Citrulline

<400> SEQUENCE: 11

Phe Xaa Phe Leu
1

<210> SEQ ID NO 12
<211> LENGTH: 4
<212> TYPE: PRT
<213> ORGANISM: Artificial Sequence
<220> FEATURE:
<223> OTHER INFORMATION: tetrapeptide
<220> FEATURE:
<221> NAME/KEY: MISC_FEATURE
<222> LOCATION: (2)..(2)
<223> OTHER INFORMATION: Xaa = Citrulline

<400> SEQUENCE: 12

Phe Xaa Phe Pro
1

<210> SEQ ID NO 13
<211> LENGTH: 4
<212> TYPE: PRT
<213> ORGANISM: Artificial Sequence
<220> FEATURE:
<223> OTHER INFORMATION: tetrapeptide
<220> FEATURE:
<221> NAME/KEY: MISC_FEATURE
```

```
<222> LOCATION: (2)..(2)
<223> OTHER INFORMATION: Xaa = Citrulline

<400> SEQUENCE: 13

Phe Xaa Val Pro
1

<210> SEQ ID NO 14
<211> LENGTH: 4
<212> TYPE: PRT
<213> ORGANISM: Artificial Sequence
<220> FEATURE:
<223> OTHER INFORMATION: tetrapeptide

<400> SEQUENCE: 14

Phe Asp Phe Pro
1

<210> SEQ ID NO 15
<211> LENGTH: 4
<212> TYPE: PRT
<213> ORGANISM: Artificial Sequence
<220> FEATURE:
<223> OTHER INFORMATION: tetrapeptide

<400> SEQUENCE: 15

Phe Lys Phe Leu
1

<210> SEQ ID NO 16
<211> LENGTH: 4
<212> TYPE: PRT
<213> ORGANISM: Artificial Sequence
<220> FEATURE:
<223> OTHER INFORMATION: tetrapeptide

<400> SEQUENCE: 16

Phe Lys Phe Pro
1

<210> SEQ ID NO 17
<211> LENGTH: 4
<212> TYPE: PRT
<213> ORGANISM: Artificial Sequence
<220> FEATURE:
<223> OTHER INFORMATION: tetrapeptide

<400> SEQUENCE: 17

Phe Asn Phe Pro
1

<210> SEQ ID NO 18
<211> LENGTH: 4
<212> TYPE: PRT
<213> ORGANISM: Artificial Sequence
<220> FEATURE:
<223> OTHER INFORMATION: tetrapeptide

<400> SEQUENCE: 18

Gly Phe Leu Gly
1

<210> SEQ ID NO 19
<211> LENGTH: 4
<212> TYPE: PRT
<213> ORGANISM: Artificial Sequence
<220> FEATURE:
```

```
<223> OTHER INFORMATION: tetrapeptide
<220> FEATURE:
<221> NAME/KEY: MISC_FEATURE
<222> LOCATION: (2)..(2)
<223> OTHER INFORMATION: Xaa = Citrulline

<400> SEQUENCE: 19

Val Xaa Phe Pro
1
```